United States Patent
Matsui

(10) Patent No.: US 7,368,713 B2
(45) Date of Patent: May 6, 2008

(54) METHOD AND APPARATUS FOR INSPECTING SEMICONDUCTOR DEVICE

(75) Inventor: Miyako Matsui, Kokubunji (JP)

(73) Assignee: Hitachi High-Technologies Corporation, Tokyo (JP)

( * ) Notice: Subject to any disclaimer, the term of this patent is extended or adjusted under 35 U.S.C. 154(b) by 195 days.

(21) Appl. No.: 11/189,898

(22) Filed: Jul. 27, 2005

(65) Prior Publication Data

US 2006/0043292 A1    Mar. 2, 2006

(30) Foreign Application Priority Data

Aug. 25, 2004    (JP) .............................. 2004-244546

(51) Int. Cl.
*G21K 7/00*      (2006.01)
*G01N 23/203*    (2006.01)
*G01N 23/225*    (2006.01)
*H01J 37/28*     (2006.01)

(52) U.S. Cl. .................. 250/310; 250/311; 250/396 R; 250/397; 250/399; 250/492.2; 250/492.3

(58) Field of Classification Search ................. 250/310
See application file for complete search history.

(56) References Cited

U.S. PATENT DOCUMENTS

| | | | | |
|---|---|---|---|---|
| 4,910,398 A | * | 3/1990 | Komatsu et al. | 250/307 |
| 5,412,210 A | * | 5/1995 | Todokoro et al. | 250/310 |
| 5,481,109 A | * | 1/1996 | Ninomiya et al. | 250/310 |
| 5,594,245 A | * | 1/1997 | Todokoro et al. | 250/310 |
| 5,866,904 A | * | 2/1999 | Todokoro et al. | 250/310 |
| 5,969,357 A | * | 10/1999 | Todokoro et al. | 250/310 |
| 6,114,695 A | * | 9/2000 | Todokoro et al. | 250/310 |
| 6,559,662 B1 | * | 5/2003 | Yamada et al. | 324/751 |
| 6,753,524 B2 | * | 6/2004 | Matsui et al. | 250/310 |
| 6,756,590 B2 | * | 6/2004 | Kazui et al. | 250/310 |
| 6,963,067 B2 | * | 11/2005 | Takeuchi et al. | 250/310 |
| 6,984,589 B2 | * | 1/2006 | Tanaka et al. | 438/714 |
| 7,049,589 B2 | * | 5/2006 | Yamaguchi et al. | 250/310 |
| 7,164,128 B2 | * | 1/2007 | Miyamoto et al. | 250/311 |
| 2003/0094572 A1 | * | 5/2003 | Matsui et al. | 250/310 |

(Continued)

FOREIGN PATENT DOCUMENTS

JP    4-149944    5/1992

(Continued)

*Primary Examiner*—Jack I. Berman
*Assistant Examiner*—Bernard Souw
(74) *Attorney, Agent, or Firm*—Antonelli, Terry, Stout & Kraus, LLP.

(57) ABSTRACT

A method and apparatus for inspecting a wafer during a semiconductor device fabrication process. The apparatus performs, only via observation from the wafer's top surface, inspection and quantitative evaluation of a portion that is in the shadow of an incident electron beam and a buried structure in the wafer. To this end, the electron beam is emitted so that it partially penetrates a wafer surface and reaches an unexposed pattern portion to the beam. When a stereoscopic structure is constructed from the scan image based on a secondarily generated signal, generate a stereoscopic model of a pattern being tested. The secondary signal is used to detect position information of a pattern edge(s) and signal intensity. Then, use the information to calculate more than one feature quantity of the test pattern. From the calculated feature quantities, the stereoscopic structure is constructed for displaying a 3D structure of the pattern.

9 Claims, 22 Drawing Sheets

U.S. PATENT DOCUMENTS

| | | | |
|---|---|---|---|
| 2003/0197873 A1* | 10/2003 | Kazui et al. | 356/625 |
| 2004/0164243 A1* | 8/2004 | Kazui et al. | 250/310 |
| 2004/0188611 A1* | 9/2004 | Takeuchi et al. | 250/310 |
| 2004/0264764 A1* | 12/2004 | Kochi et al. | 382/154 |
| 2005/0133718 A1* | 6/2005 | Miyamoto et al. | 250/307 |
| 2005/0285034 A1* | 12/2005 | Tanaka et al. | 250/310 |
| 2006/0043292 A1* | 3/2006 | Matsui | 250/310 |
| 2007/0114398 A1* | 5/2007 | Miyamoto et al. | 250/307 |

FOREIGN PATENT DOCUMENTS

| | | |
|---|---|---|
| JP | 5-290786 | 11/1993 |
| JP | 7-27549 | 1/1995 |

* cited by examiner

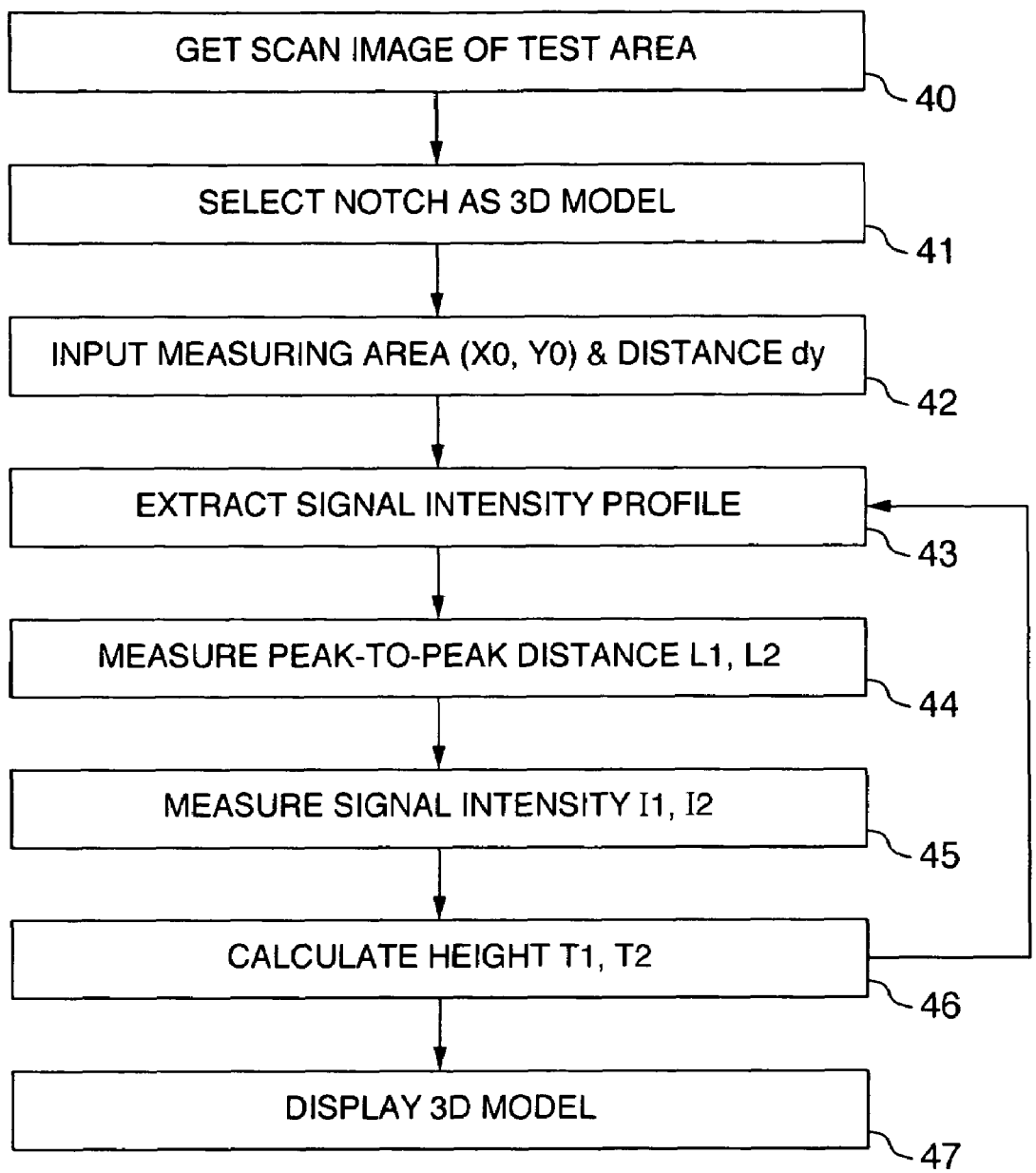

METHOD AND APPARATUS FOR INSPECTING SEMICONDUCTOR DEVICE

INCORPORATION BY REFERENCE

The present application claims priority from Japanese application JP 2004-244546 filed on Aug. 25, 2004, the content of which is hereby incorporated by reference into this application.

BACKGROUND OF THE INVENTION

1. Field of the Invention

The present invention relates to substrate inspection technologies using scanning electron microscope equipment and electron rays. More particularly, this invention relates to an inspection technique for performing, on a substrate such as a semiconductor wafer or a reticle having a fine pattern, metrology of such fine pattern which is formed at a reverse tapered shape or within a substrate surface and for detecting defects, if any.

2. Description of the Related Art

In a scanning electron microscope (SEM), there is widely used a method for scanning an electron beam to permit it fall onto a workpiece and for detecting secondarily obtainable secondary electrons and reflected or "back-scattered" electrons to thereby obtain a scan image (also known as SEM image). Traditionally, the size measurement of an ultrafine pattern such as a semiconductor device or the like has been performed while using as an incident electron ray an electron beam with its energy ranging from several hundred of eV to several keV.

However, in such the low-acceleration SEM, while it is possible to observe those portions being directly irradiated with the electron beam, it is unable to observe shadow portions that are created by the presence of step-like differences of a workpiece surface, resulting in the lack of an ability to perform the size measurement. For example, in the prior art low-acceleration SEM, in case where an upper face 23 of an opening is less in dimension than its bottom portion 24 as shown in FIG. 2A, what can be done is merely to perform observation and measurement of the shape of the opening's upper face 23 as in a scan image shown in FIG. 2B. Accordingly, in order to measure the size of the opening bottom face 24, it was required to cut the workpiece into portions for formation of a cross-section and then observe a shape from the cross-section. Alternatively, as shown in FIG. 3A, even when an attempt is made to measure an inter-wire distance size 28 between an electrical wiring line or lead 26 on a substrate surface and a wire lead 27 buried within the substrate, what can be measured by the low-acceleration SEM is only the wire 26 on the substrate surface so that it has been impossible to measure the distance between the wires.

A method for solving this problem and for observing/measuring an internal structure of a workpiece without having to cut the workpiece is disclosed, for example, in JP-A-7-27549. A technique as taught thereby is designed to emit an electron beam 6 which has its energy capable of penetrating part of a workpiece and reaching a portion that is not exposed with respect to the incident electron beam, and then use a scan image obtained from a secondarily generated signal to perform size measurement. Using this scheme makes it possible, at the opening such as shown in FIG. 2A, to perform size measurement of the structure of the opening bottom face 22—this face becomes a shadow of the incident electron beam and, for this reason, cannot be measured by the low-acceleration SEM—and observation of the structure of the intra-substrate wiring lead 27 and its size 28 without forming a cross-section of the workpiece.

With noticeable advances in miniaturization of semiconductor devices in recent years, ultra-fine or "micro" structure measurement increases in importance. Especially, gate shapes are becoming finer and more complicated. Depending upon whether they are manufactured successfully or not, device performance and production yield are affectable significantly. Consequently, a three-dimensional measurement technique for use with such gate structures is becoming more important. For instance, in order to lessen a gate length, there is used a structure which has a gate electrode 29 with its bottom portion 30 being narrower than an upper portion 31 as shown in FIG. 4. As the low-acceleration SEM is such that only the shape of a top surface is obtainable, a size 32 of the bottom portion is not measurable.

For example, when observing the gate electrode 29 with its cross-sectional structure shown in FIG. 4 by use of the prior art low-acceleration SEM, what can be observed is merely the shape of the upper part 31 of the gate electrode as shown in a scan image of FIG. 5. Also note that in the prior art low-acceleration SEM, there was a method of performing observation by emitting an electron beam from an oblique direction to permit the electron beam to fall onto a "shadowed" portion. Unfortunately, the method for obliquely emitting the electron beam requires the image processing for recreation or reconstruction of a stereoscopic structure from the scan image thus obtained, resulting in occurrence of a problem as to deterioration of accuracy. Alternatively, in the case of a high-density pattern, it is no longer possible to irradiate the electron beam to the bottom 30 of the gate electrode due to the fact that it lies in a shadow of its neighboring pattern. This makes it impossible to perform any intended observation.

Additionally with the prior art low-acceleration SEM, it was merely possible, in a gate having an inverted taper shape, to observe only the shape of the gate electrode upper portion 31. Thus it was unable to measure the width 32 and taper angle 33 of the gate electrode.

Regarding semiconductor device manufacturing methodology, there is known a semiconductor fabrication method having the steps of forming a spacer 35 on a gate electrode 34 as shown in FIG. 6D, and thereafter performing ion implantation (referred to as implantation hereinafter) to thereby form a junction(s) in a substrate. For example, after having formed a pattern of the gate electrode 34 as shown in FIG. 6A, implantation 36 is performed with the gate electrode 34 being as a mask, thereby forming a junction 37 in the substrate as shown in FIG. 6B. Thereafter, a spacer 35 is formed on the gate electrode 34 as shown in FIG. 6C. Then, as shown in FIG. 6C, implantation 38 is carried out with the spacer 35 as a mask, thereby forming a junction 39 as shown in FIG. 6D. In a device with such the structure, precise measurement of the structure of the gate electrode 34 and spacer 35 enables judgment of whether the device is good or bad and also prediction of the performance thereof.

However, in the prior art low-acceleration SEM, as shown in FIG. 7, only the spacer 35 and the substrate 25 are observable, and what is knowable is merely the shape of a top surface of the device. It was unable to observe any relative structure of the gate electrode 34 and the spacer 35. In the prior art, in order to observe both the gate electrode 34 and the spacer 35 at a time, it was necessary to destroy part of a workpiece for formation of a cross-section and then observe it. With this method, destruction of the workpiece was inevitable. Another problem faced with this method is an inability to measure any feature quantity that determines the device performance.

On the other hand, with the technique disclosed in JP-A-7-27549, a hole-like shape with the presence of a portion that becomes the shadow of an incoming electron beam is measured. However, the invention disclosed in JP-A-7-27549 suffers from a problem which follows: it fails to offer the capability of measuring those feature quantities required for three-dimensional (3D) measurement. The feature quantities required for the 3D measurement refer to certain information necessary for the prediction of a stereoscopic structure, such as pattern height information or the like, by way of example. Accordingly, in the invention recited in the JP-A-7-27549 document, when performing 3D measurement, the hole shape is obtained, for example, by acquiring a scan image while rotating a workpiece support stage and letting an incident beam fall along an oblique direction onto a target pattern as mounted thereon. This is because any 3D structure could not be accurately calculated from the information of secondary signal intensity, although those sizes being displayed in the scan image are measurable in the prior art.

Although it is also possible to tilt the incident beam by means of a technique for slanting the stage, this raises a need for acquiring a scan image while slanting or sloping the stage. This causes a problem as to the necessity of varying the stage angle in a way pursuant to the shape of a pattern to be inspected. In addition, in case the inspection pattern is complicate in shape, the resulting scan image becomes complicated. This leads to a problem that the image analysis for obtaining a stereoscopic structure becomes more difficult.

SUMMARY OF THE INVENTION

It is therefore an object of the present invention to provide an improved method and apparatus for emitting an electron beam onto a workpiece to be inspected to thereby observe not only the surface shape of a pattern but also the shapes of a shadowed portion and a buried pattern, and for using both the position information of a secondary signal thus obtained and the signal intensity to calculate a stereoscopic structure of the pattern, thereby automatically measuring one or more feature quantities that affect the device characteristics.

According to this invention, in a semiconductor device inspection apparatus having a means for emitting an electron beam which penetrates part of an object to be observed and which is capable of reaching an unexposed portion with respect to the electron beam, a means for detecting a signal that is secondarily generated from a portion being irradiated with the electron beam, a means for generating a scan image of a length measurement object based on the secondary signal, and a length measurement function of performing size measurement based on the scan image, there is provided a means for extracting a signal profile from the scan image thus obtained, for extracting the position information of a pattern and the signal intensity, for generating a stereoscopic model of the pattern, for using the extracted position information and signal intensity to calculate a three-dimensional feature quantity of the pattern being inspected, for constructing a stereoscopic structure from the calculated feature quantity of the pattern, and for visually displaying this stereoscopic model and any given cross-section of the stereoscopic model and also wafer in-plane distribution. Also provided is a means for displaying information such as the position and line width or else of the observation object, which are out of allowable values with the calculated pattern's feature quantity being set therein.

With the use of this invention, in the semiconductor device inspection apparatus having length measurement functions for emitting an electron beam capable of reaching an unexposed portion with respect to the electron beam and for detecting a signal that is secondarily generated from an irradiation part of the electron beam, it becomes possible not only to perform length measurement of the width in a lateral direction of the pattern but also to calculate height information to thereby evaluate the stereoscopic structure. In addition, it becomes possible to display a given cross-section of the stereoscopic structure thus calculated. For example, it becomes possible to simultaneously measure both the line width on a top surface of the object being observed and the line width of a concave portion; furthermore, it is possible to calculate the depth of such concave portion within the workpiece, thus enabling evaluation of the stereoscopic structure. Additionally, even for a pattern having a taper angle, it is possible to calculate the taper angle and then display it.

In addition, it becomes possible to measure from the same scan image both an edge of the pattern to be inspected and the position of an edge of the pattern being buried within the observation object and calculate a stereoscopic structure from the measured pattern information and then display any given cross-section. Further, it becomes possible to display the information such as the measured position and line width or else of the observation object and then perform alarm display of a pattern which is out of a preset allowable value. Additionally, by performing inspection by this scheme prior to an anneal processing for activating dopants implanted, it is possible to recover or "cure" damages due to electron ray irradiation.

As a result of this, it becomes possible to quickly grasp the feature quantity that contributes to the device characteristics, thereby enabling quick start-up of a semiconductor device fabrication process. In addition, applying this scheme to semiconductor fabrication processes makes it possible to promptly discover process abnormality, thereby enabling early improvement of manufacturing yields.

Other objects, features and advantages of the invention will become apparent from the following description of the embodiments of the invention taken in conjunction with the accompanying drawings.

BRIEF DESCRIPTION OF THE DRAWINGS

FIG. 11 is one example of a flow for generating a stereoscopic model of the notch shape according to the invention.

DETAILED DESCRIPTION OF THE EMBODIMENTS

Embodiment 1

In this embodiment, there will be explained one example of a method for inspecting a pattern having its shape with a notch formed in a gate electrode or the like. Note here that the notch of the gate electrode refers to a certain portion in which the width of a lower bottom part of the gate electrode is smaller than an upper bottom thereof. The gate electrode with such the notch defined therein is used from time to time in high-speed devices in order to make the gate length smaller than the limit of lithography.

Figure 1:
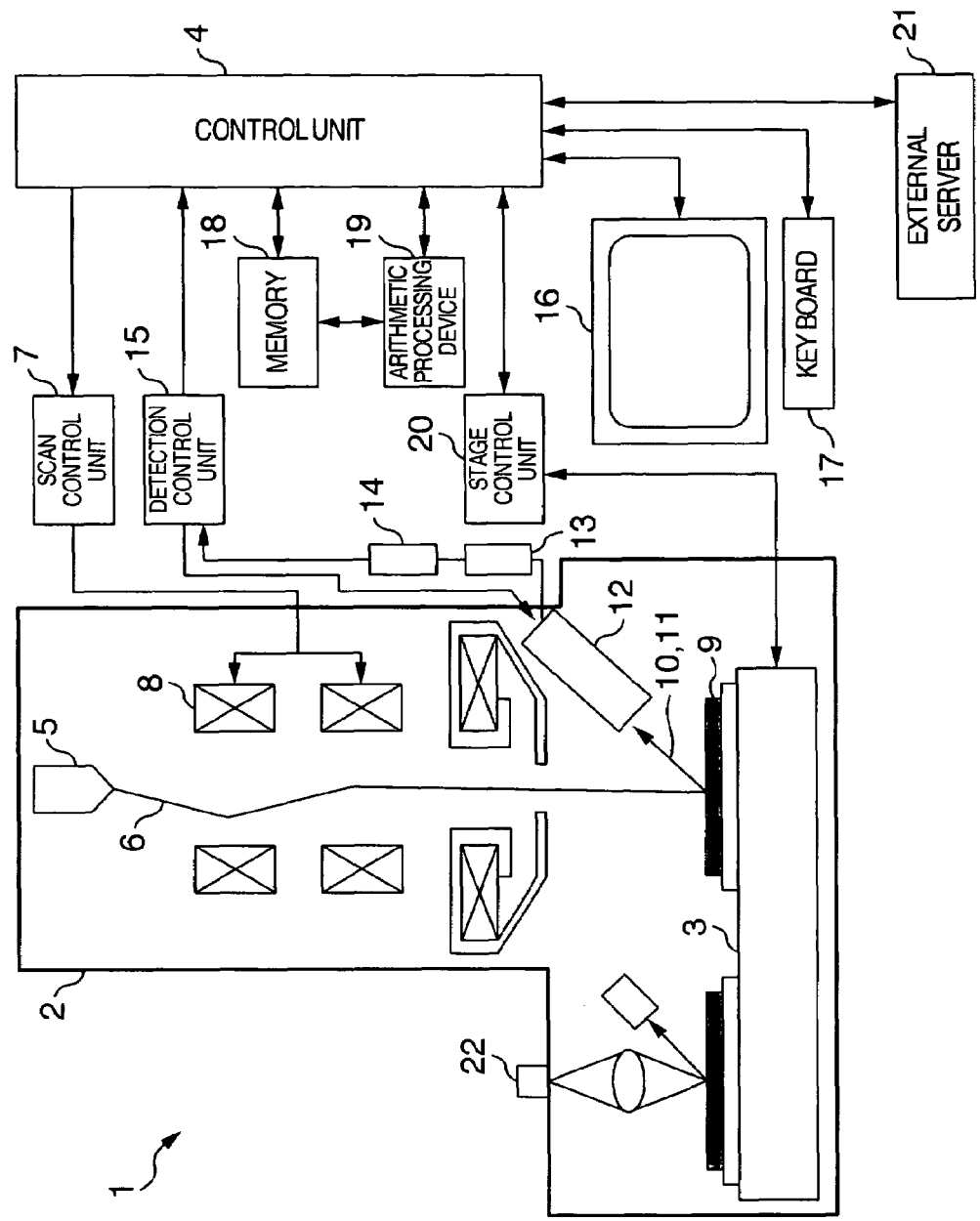
FIG. 1 is a diagram showing an exemplary configuration of a semiconductor device inspection apparatus used in the present invention.
Figure 2A:
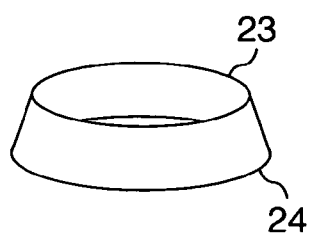
FIGS. 2A and 2B are explanation diagrams showing one example of the observation using prior known low-acceleration SEM.
Figure 2B:
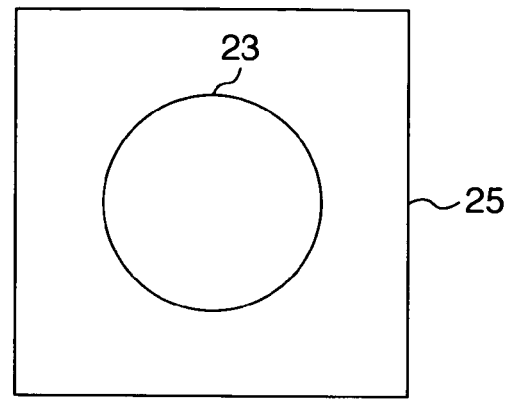
Figure 3A:
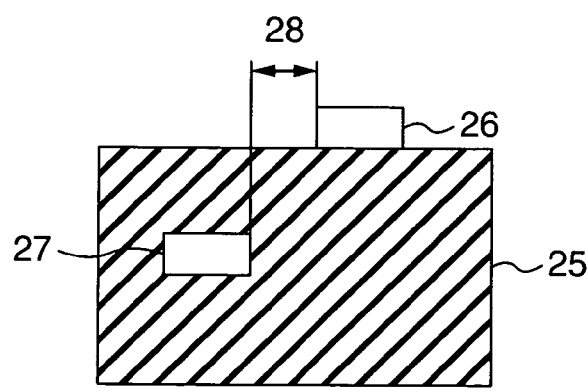
FIGS. 3A and 3B are explanation diagrams showing another example of the observation using the conventional low-acceleration SEM.
Figure 3B:
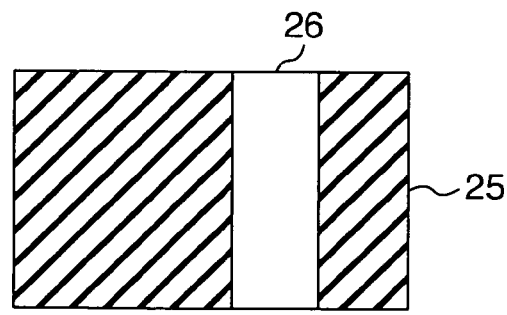
Figure 4:
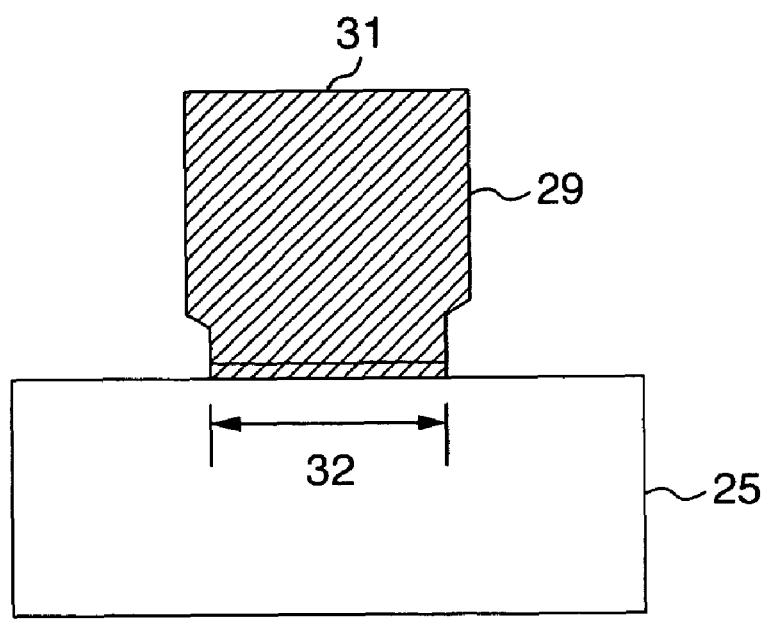
FIG. 4 is an explanation diagram showing one example of a gate structure.
Figure 5:
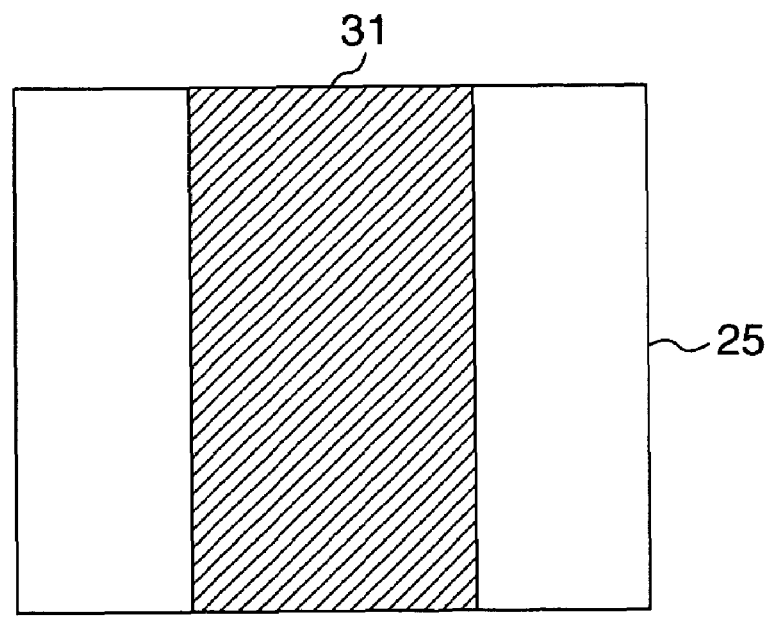
FIG. 5 is an explanation diagram showing one example of a scan image of the gate structure by means of the prior art low-acceleration SEM.
Figure 6A:
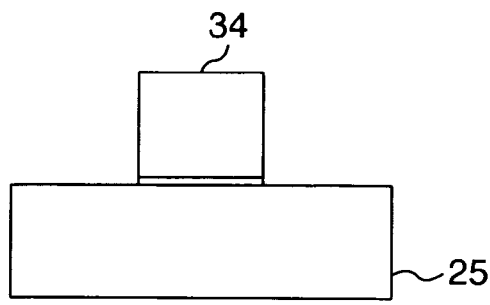
FIGS. 6A to 6D are explanation diagrams each showing one example of a manufacturing process of a spacer-added gate structure.
Figure 6B:
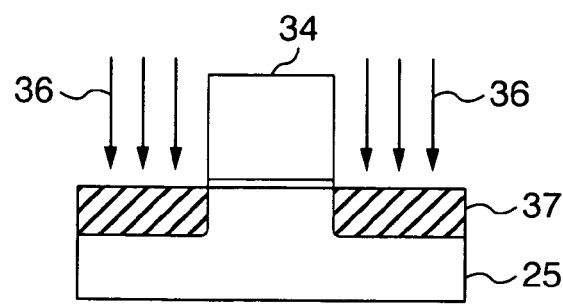
Figure 6C:
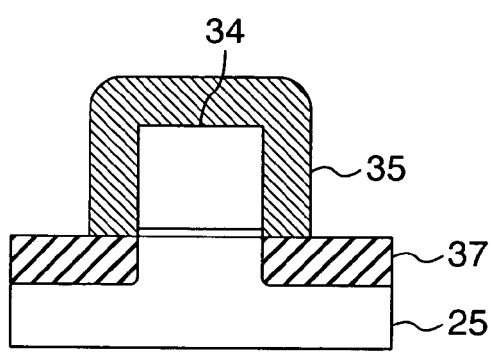
Figure 6D:
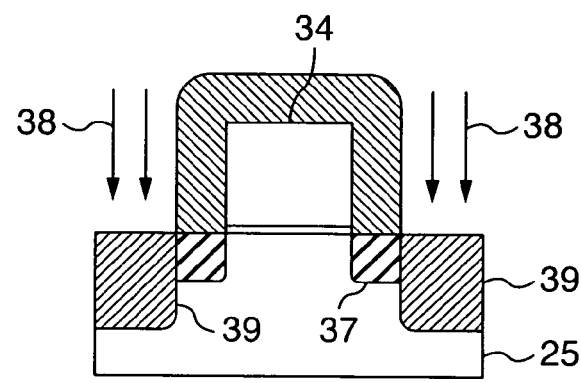
Figure 7:
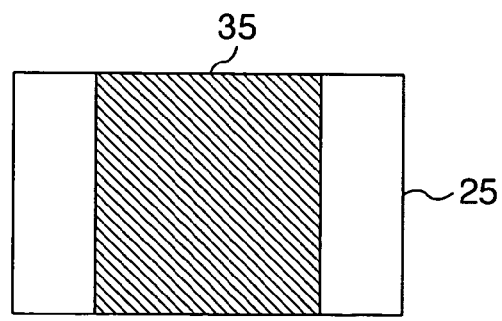
FIG. 7 is an explanation diagram showing one example of a scan image of a spacer-added gate structure due to the prior art low-acceleration SEM.

Referring to FIG. 1, there is shown in block diagram form a configuration of a semiconductor device inspection apparatus used in this invention. An electron beam 6 of high energy, which is emitted from an electron source 5, is deflected by a scanning coil 8 under the control of a scan control unit 7 and is then raster-scanned on a wafer 9. The scanning range of the electron beam 6 on the wafer 9 is determined by appropriately setting an output of the scan control unit 7 on the basis of a magnification which is input in advance from a user interface unit including a keyboard 17. The wafer 9 is settled on a movable stage 3. The stage 3 is controlled by a stage control unit 20 in motion to each direction. A secondarily generated signal of secondary electrons 10 and reflected or "back-scattered" electrons 11 or else, which are generated from a surface of the wafer 9 due to the scanning of the electron beam 6, is detected by a detector 12 and then amplified by an amplifier unit 13. The amplified secondary signal is converted by a converter 14 into a string of digital data, which is sent forth toward a control unit 4 and visually displayed as a scan image on a monitor 16 and then stored in a memory 18. An arithmetic processing device 19 is operable to read the image information in the memory 18 and then recognize a position to be subjected to the length measurement. It should be noted that in case the workpiece stage 3 includes a rotation mechanism, it is possible to reflect an angle of rotation on a stereoscopic model of an object being inspected.

Figure 8A:
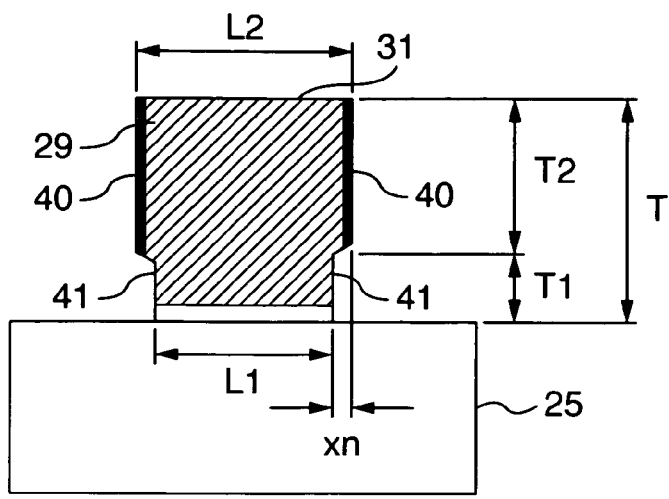
FIGS. 8A to 8C are explanation diagrams showing one example of an observation method of a notch shape in accordance with this invention.
Figure 8B:
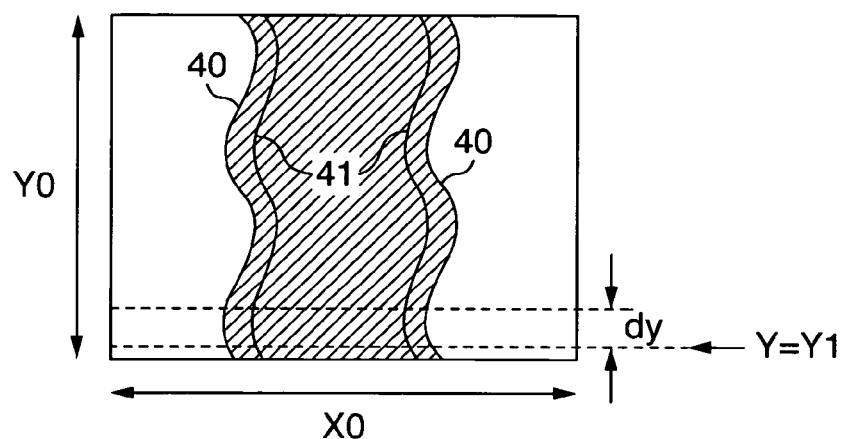

An explanation will now be given of principles of an observation technique using the electron beam 6 of high energy. When letting the high-energy electron beam 6 fall onto a wafer 9 such as the one shown in FIG. 8A, secondary electrons 10 and backscattered electrons 11 generate from the substrate surface, while a large number of secondary electrons 10 and backscatter electrons 11 are generated by the so-called "edge effect" from a pattern sidewall(s) 40. In addition, due to an incident electron beam 35 which has penetrated a top surface of the wafer, a large number of secondary electrons 10 and backscatter electrons 11 are generated by the edge effect from a notch portion 41 of the pattern, also. When forming a scan image of the pattern of FIG. 8A from the signals of these secondary electrons 10 and backscatter electrons 11, the pattern's sidewall edges 40 and notch 41 were observed brightly as shown in FIG. 8B. Thus, it becomes possible to simultaneously perform length measurement of both a line width L2 of the pattern on the substrate surface and a line width L1 of the pattern at the notch portion thereof.

Next, one example of a method for generating a stereoscopic model from the scan image shown in FIG. 8B will be explained in accordance with a flow chart shown in FIG. 11. In this embodiment, an explanation will be given of one example of the length measurement method of the notch shape shown in FIG. 8A. Algorithm for control of the flow of FIG. 11 is stored as a software program in the memory 18 shown in FIG. 1 or in an external data storage device (not shown), or alternatively in a storage means provided in an external server 21, and is expanded into and processed by the arithmetic processor means 19 in adequate events.

Firstly, input scan image acquiring conditions, including but not limited to a region or area to be observed and observation position; then, obtain a scan image of the observation area (at step 40 of FIG. 11). A database of stereoscopic models is stored in the memory 18 shown in FIG. 1 or in an external storage device (not shown) or in a storage means within the external server 21, and is expanded to and processed by the arithmetic processor means 19 when the need arises.

Figure 8C:
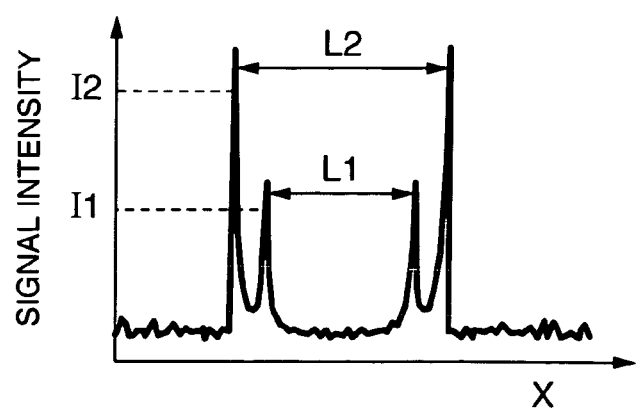
Figure 9A:
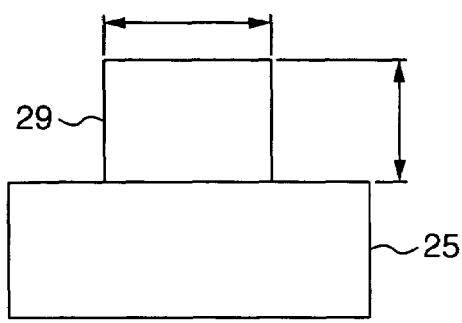
FIGS. 9A through 9D are explanation diagrams each showing one example of a stereoscopic model of the invention.
Figure 9B:
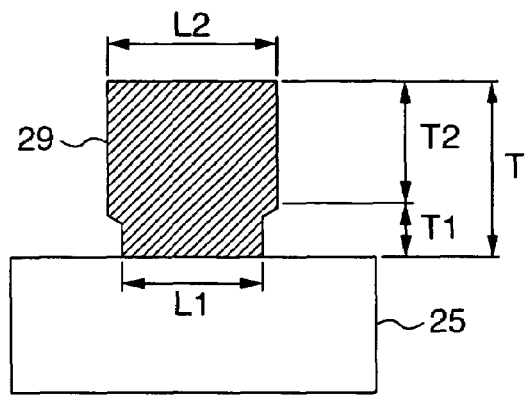

Next, select the kind of a stereoscopic model of the pattern observed. Selectable examples of the stereoscopic model kind may typically include a rectangular solid such as shown in FIG. 9A, a notch shape shown in FIG. 9B, an inverted taper shape shown in FIG. 9C, and a buried electrode structure shown in FIG. 9D. In this embodiment, the notch shape shown in FIG. 9B is selected as the kind of the stereoscopic model (at step 41). Upon inputting of the length measurement range (X0, Y0) and an interval or distance "dy" for length measurement (at step 42), a profile of signal intensity at Y=Y1 as shown in FIG. 8B is extracted into the arithmetic processor device 19 as shown in FIG. 8C (at step 43).

For use as this profile of the signal intensity, an average value of several nearby lines in the scan image may be employed. Additionally, noise removal/elimination processing and averaging processing may be done by prior known methods. From this profile, a distance between two outside peaks selected from four peaks observed is length-measured to thereby obtain the line width L2 on the top surface of the substrate. In addition, a distance between two inside peaks is measured, thereby obtaining the line width L1 at the notch portion (at step 44). Further, the signal intensity I2 at an outside location of the pattern and the signal intensity I1 at the notch are measured (at step 45). Then, input the pattern's height T. Thus it was possible to obtain the height T1 that spans from the notch's upper part to the bottom face of a concave portion along with the height T2 of from the notch upper part to the top surface (at step 46).

Figure 10:
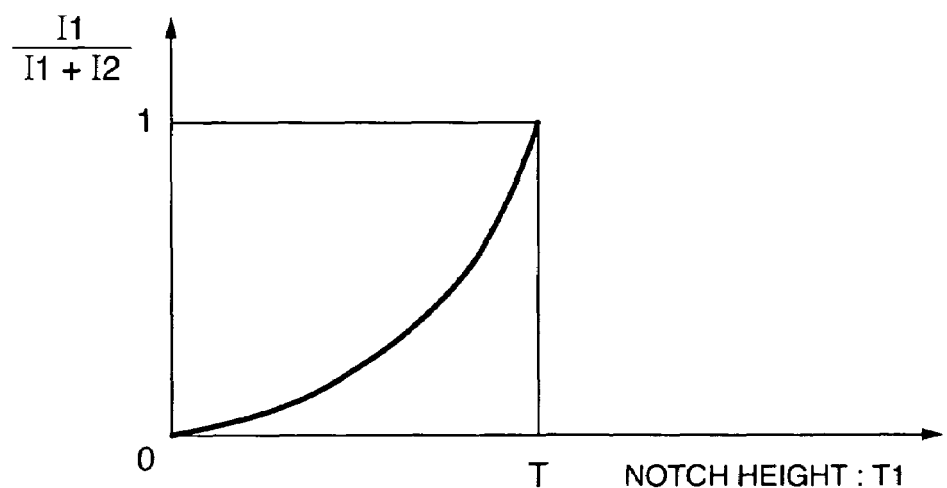
FIG. 10 is an explanation diagram showing a relationship of the height of a notch used in the invention, a signal intensity I2 of a peak for determination of a line width L2 at the uppermost surface of a pattern, and a signal intensity I1 of a notch portion 41.

An explanation will here be given of a method for calculating, from the scan image, the height T1 spanning from the notch's upper part up to the concave bottom face and the height T2 of from the notch upper part to the top surface. From the scan image, the height T1 of from the notch upper part to the concave bottom face and the height T2 from the notch upper part to the top surface are obtainable based on a relationship between the signal intensity I2 of a peak that determines the line width L2 on the top substrate surface of the pattern and the signal intensity I1 of the notch portion 41 in view of a relationship shown in FIG. 10. The relation of FIG. 10 is obtained by Monte Carlo simulation. The signal intensity I2 of the pattern outside is variable depending upon the length T2, while the signal intensity I1 of the notch is dependent on T1. Also note that the signal intensity I1 of the notch decreases in a way depending on a notch amount "xn" and a thickness T2 of a layer above the notch. Whereby, the signal intensity I1 of the notch and the signal intensity I2 of the pattern outside may be represented by the equations which follow:

$$I1 = I \cdot T1/T \exp(-B \cdot xn)\exp(-A \cdot T2) \quad (1)$$

$$I2 = I \cdot T2/T + C \quad (2)$$

where, the constants I, A, B and C are determinable in advance by the Monte Carlo simulation or experimentation.

Figure 12A:
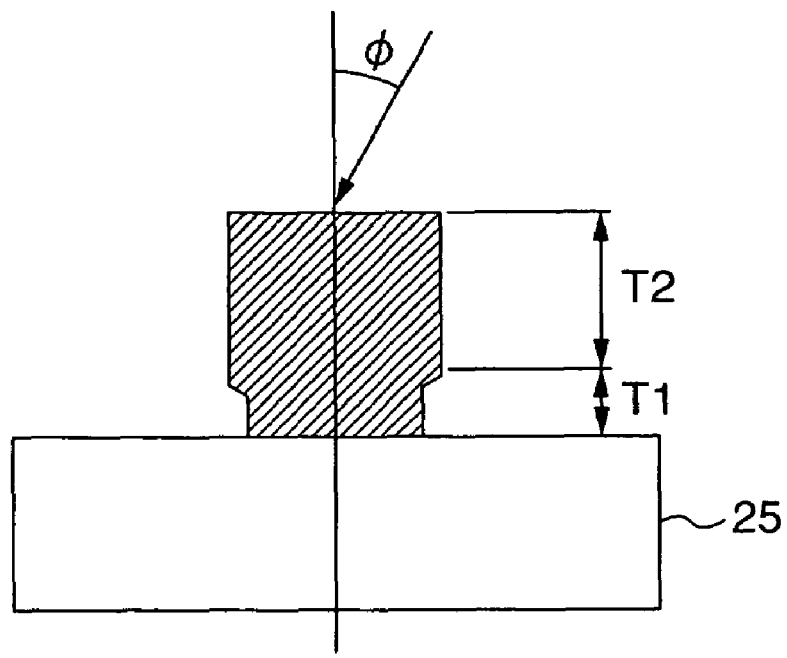
FIGS. 12A-12B are explanation diagrams showing one example of a length measurement method in the case of observation using an angle of incidence $\phi$ as used in the invention.
Figure 12B:
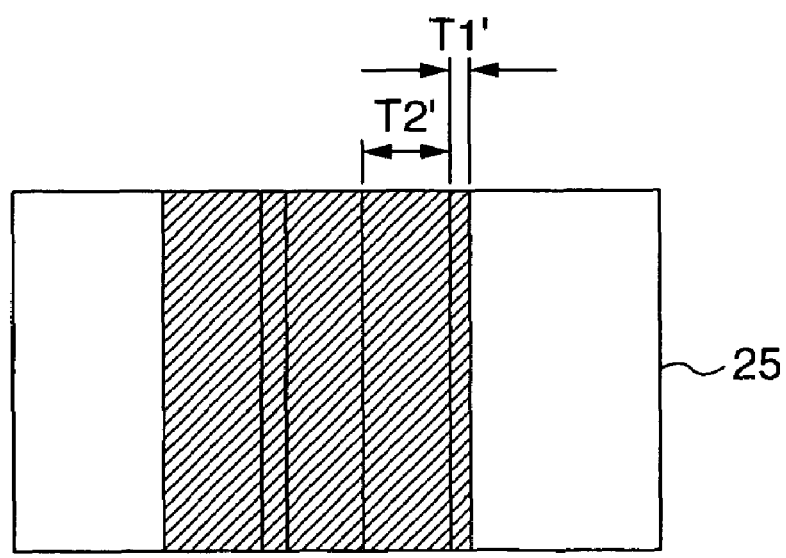
Figure 13:
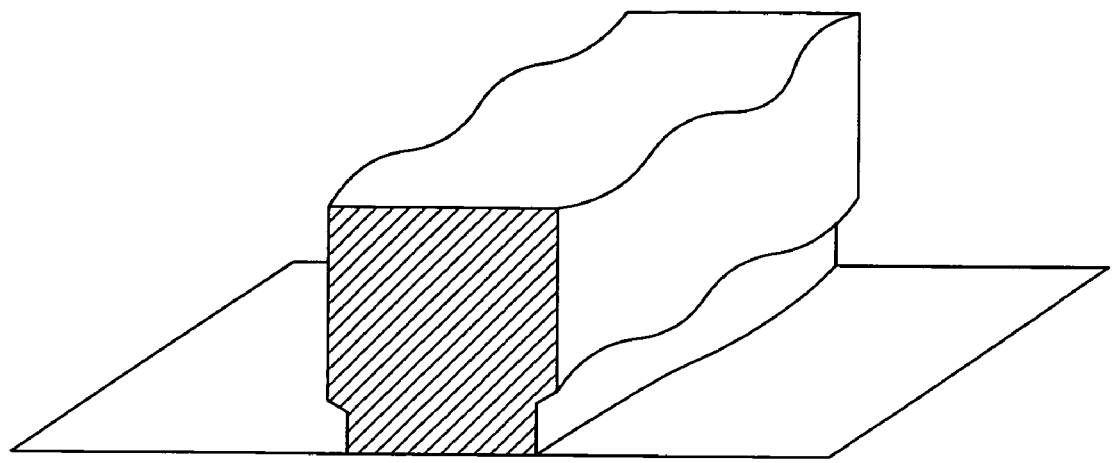
FIG. 13 is an explanation diagram showing one example of a method for displaying a stereoscopic structure with a notch shape of the invention.

As for the pattern height T, either a design value or a film thickness value measured prior to the pattern formation can also be acquired from the external server 21 or via a storage medium. Accordingly, once the values I1, I2 and xn are measured from the signal profile, it is possible to calculate T1 and T2 at the arithmetic processor device 19. Alternatively, in the case where the movable stage 3 is designed to offer rotation capabilities, the length measurement can be performed from a scan image that is obtained when emitting the electron beam 35 at an angle φ with respect to the substrate as shown in FIG. 12A. In case the scan image was acquired with the irradiation of electron beam 6 at its incidence angle φ, one or more edges of the scan image are detected as shown in FIG. 12B whereby the values T1, T2 and T can also be directly calculated from the scan image on the basis of a height T1' of a notch portion of the scan image and a length T2' of a sidewall portion of the scan image in view of the relationship of the following equations:

$$T1' = T1 \cdot \tan\theta \quad (3)$$

$$T2' = T2 \cdot \tan\theta \quad (4)$$

After having obtained the values L1, L2, T1 and T2 at Y=Y1 in this way, then extract a profile at Y=Y1+dy (at step 43 of FIG. 11).

When a stereoscopic model is obtained through repeated execution of this procedure, it is possible to visually display a stereoscopic structure on the monitor 16 in a three-dimensional (3D) way (at step 47). Furthermore, it is possible to display any given cross-sectional structure on the monitor 16. It is also possible to display a wafer in-plane distribution of the obtained feature quantities of the pattern, such as the line width L1 at the notch portion, the line width L2 on the top substrate surface, the height T1 of from the notch's upper part to the bottom face of the concave portion, and the height T2 from the notch's upper part to the top substrate surface. It is also possible to calculate an average value and a distribution value of these feature quantities for display on the monitor 16.

Figure 14:
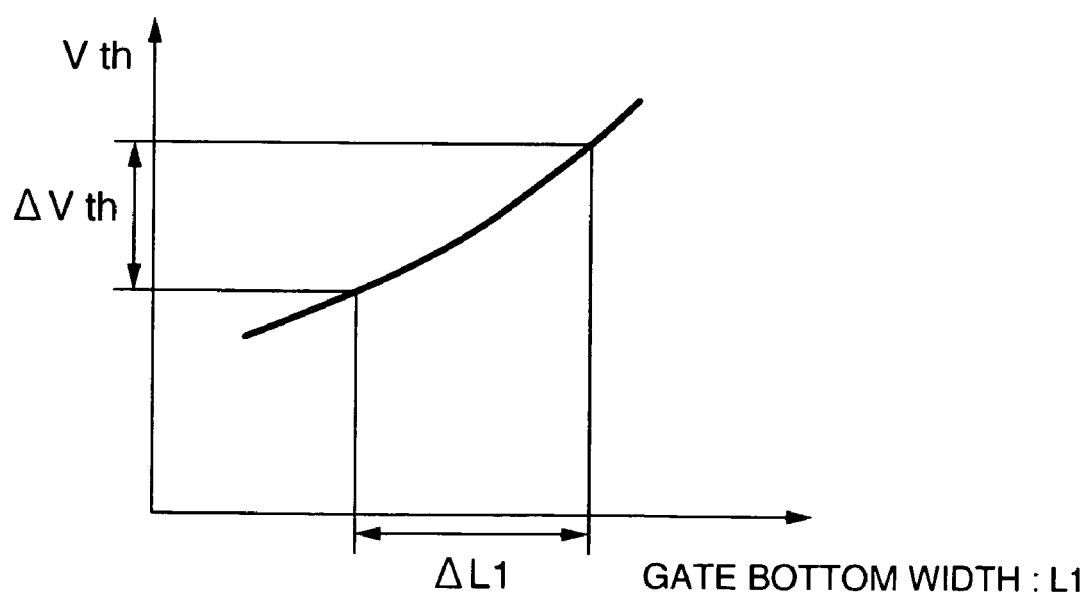
FIG. 14 is an explanation diagram showing one example of the relationship of a threshold voltage versus a width L1 of a gate electrode bottom portion of a MOS device used in the invention.

A method will next be described for performing the setup of allowable values of feature quantities in light of the correlation of these feature quantities to the semiconductor device characteristics. For example, there will be stated an example using as the semiconductor device characteristics a threshold voltage of a metal oxide semiconductor (MOS) device. See FIG. 14, which shows one example relating to the threshold value Vth of MOS device and the line width L1 of a notch portion. In a semiconductor device production line, an allowable value ΔVth of the threshold value of MOS device is used to calculate an allowable value of the line width ΔL1 at the notch. When a tested pattern exceeds at its notch portion the allowable value ΔL1 of the line width, an alarm message is displayable with or without sounds. The allowable value ΔL1 is input to the inspection apparatus via a user interface that is provided in the apparatus. Examples of the user interface include the keyboard 17 and the monitor 16 shown in FIG. 1. The input allowable value ΔL1 is stored either a register within the control unit 4 or the arithmetic processor device 19 or in the memory 18 for later reference during alarm displaying.

Additionally, this scheme should not be limited to the gate pattern of semiconductor devices and may also be applicable to the inspection and stereoscopic shape evaluation of wiring lead shapes, magnetic heads, and micro-electromechanical system (MEMS) devices.

Embodiment 2

In this embodiment, there will be explained one example of a taper angle inspection method of a pattern such as a gate electrode or the like. In this invention, the semiconductor device inspection apparatus having the configuration shown in FIG. 1 is usable. Here, the taper angle refers to an angle 33 defined by a substrate 25 and a sidewall 48 of the pattern such as a gate electrode in a cross-section of the pattern shown in FIG. 9C, which is an important parameter that determines the device characteristics.

Figure 9C:
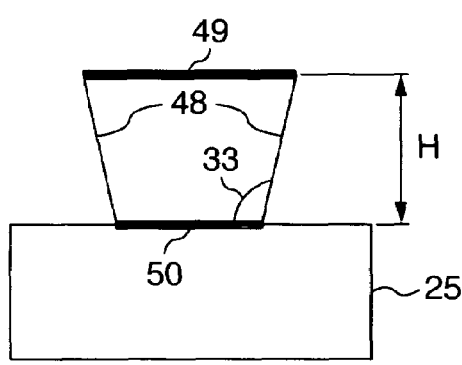

When emitting a high-energy electron beam 35 onto the pattern having the taper angle 33 as shown in FIG. 9C, secondary electrons 10 and backscattered electrons 11 are generated from the substrate surface, resulting in a large number of secondary electrons 10 and backscatter electrons 11 being generated by the edge effect from sidewalls 48 of the pattern. In case the taper angle is 90° or greater, a large number of secondary electrons 36 and backscatter electrons 37 are also generated by the edge effect from the sidewalls 48 of reverse taper, due to the irradiation of an incident electron beam 6 that has passed through a surface layer of a wafer. Additionally, those electrons which are reflected or backscattered from the pattern's bottom face attempt to enter again the sidewall 48, resulting in secondary electrons 10 being generated therefrom. When forming a scan image of the pattern of FIG. 9C from the signal of these secondary electrons 10 and backscatter electrons 11, the pattern's sidewalls 48 are brightly observed as shown in FIG. 15A.

Figure 15A:
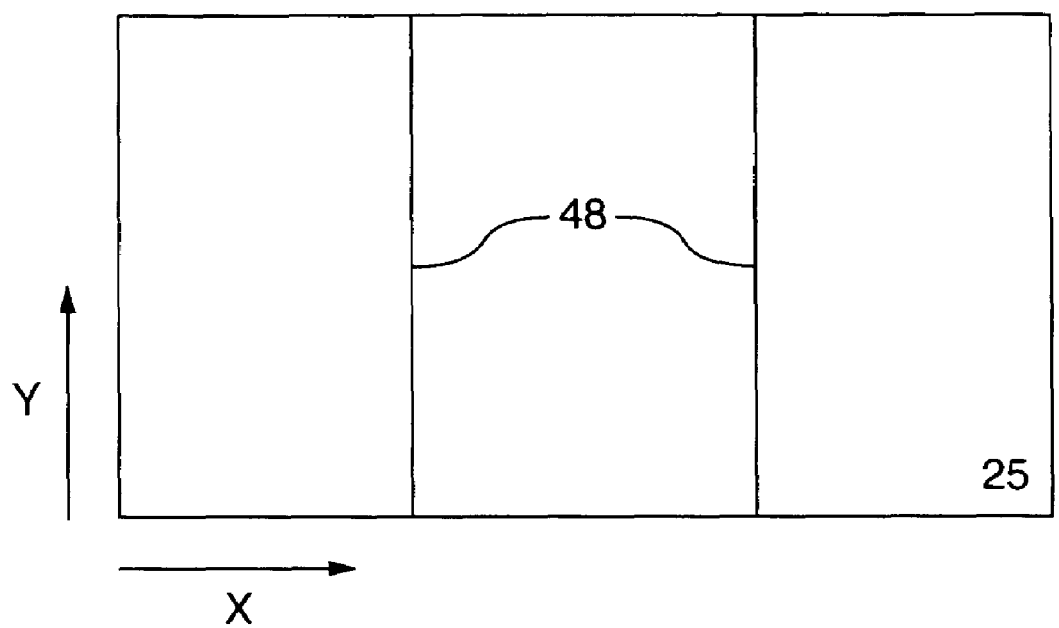
FIG. 15A depicts a scan image of a taper-shaped gate pattern used in the invention.
Figure 15B:
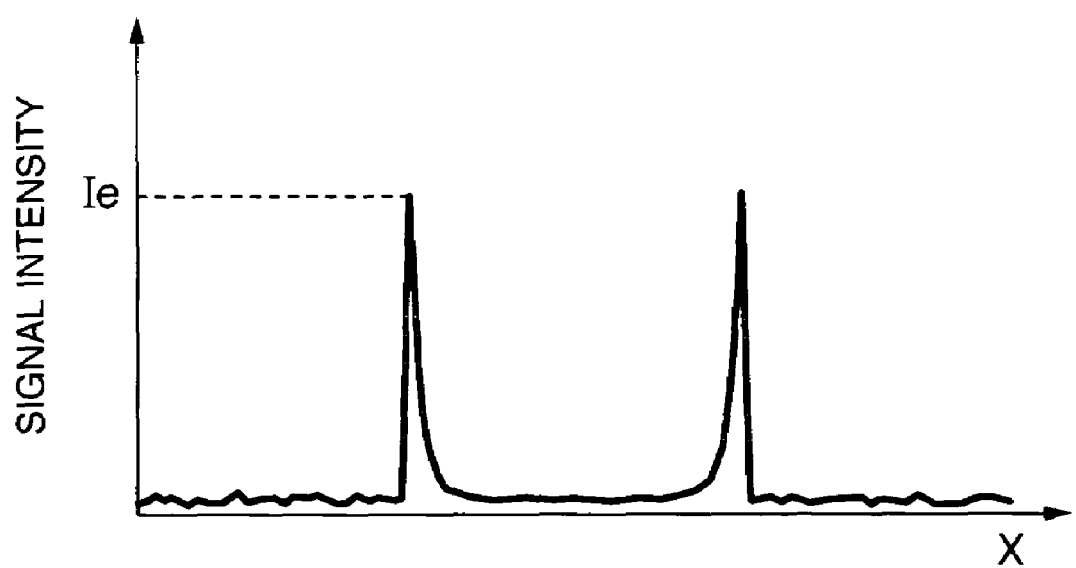
FIG. 15B shows one example of a profile of signal intensity.
Figure 16:
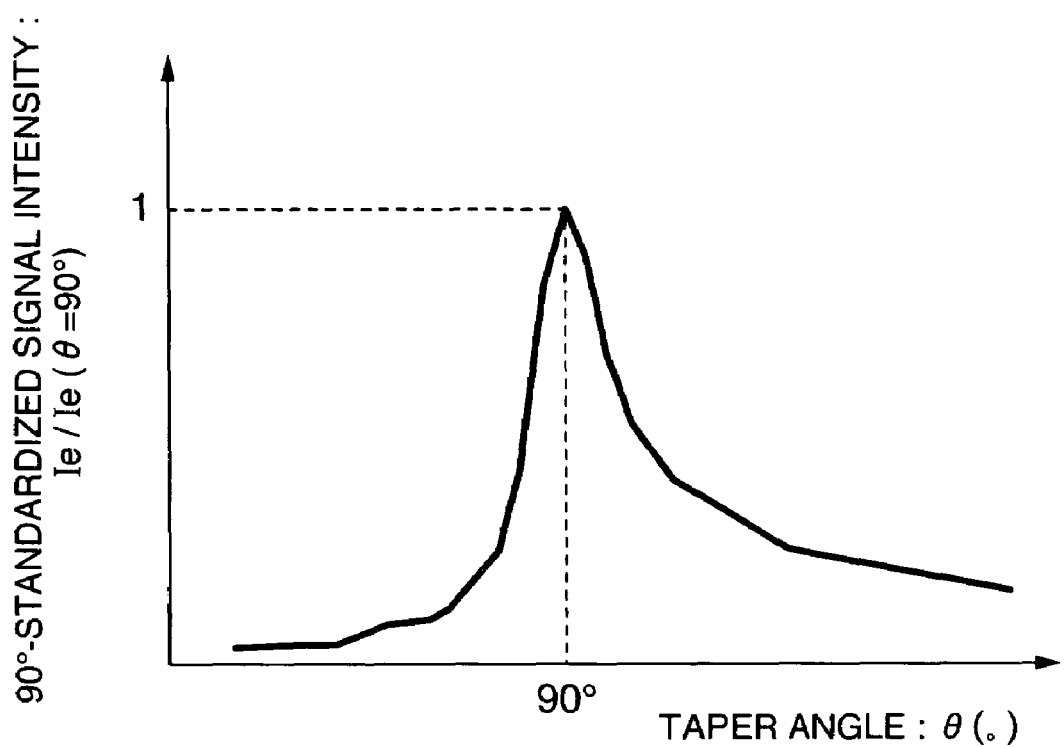
FIG. 16 is an explanation diagram showing a correlation of the signal intensity Ie of the taper shape used in the invention and a taper angle $\theta$ thereof.

A line profile of the signal intensity of the scan image shown in FIG. 15A is shown in FIG. 15B. In case the taper angle is 90° or more or less, the taper angle θ is measurable with increased sensitivity from the signal intensity of a sidewall portion 48, because the signal intensity Ie of sidewall 48 is largely dependent upon the taper angle θ. FIG. 16 shows one example of a relationship of the signal intensity Ie of an edge portion versus the taper angle θ. The signal intensity Ie of the edge of a longitudinal axis is standardized by the signal intensity of the edge portion when θ=90°. Whereby, it can be considered that the taper angle θ was varied due to a relative change of the signal intensity Ie. Thus, it becomes possible to calculate a wafer in-plane distribution of the taper angle θ from a wafer in-plane distribution of the signal intensity Ie of the edge portion and then display the distribution calculated.

Next, an explanation will be given of a method for measuring an absolute value of the taper angle θ from the signal intensity Ie of the edge portion in accordance with a flow of FIG. 19. Regarding the flow shown in FIG. 19 also, a software program of the flow control is stored in the memory 18 of FIG. 1 or in an external storage device (not shown) or alternatively in a storage means within the external server 21, and is expanded to and processed by the arithmetic processor means 19 whenever the need arises.

Figure 17:
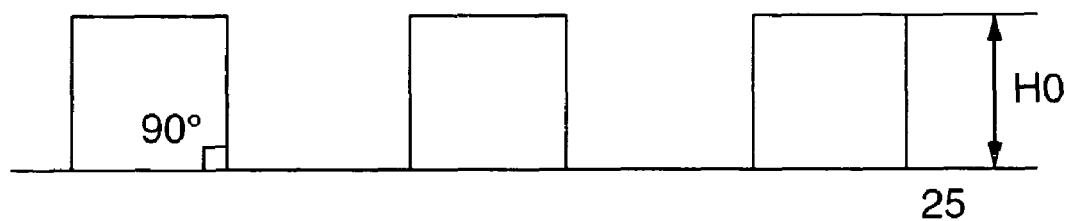
FIG. 17 is an explanation diagram showing one example of a standard workpiece used in the invention.

Note here that in the inspection apparatus 1 using an electron beam, the status of the apparatus may usually change day by day—obviously, the state of an incident electron beam and the signal detection efficiency are also variable. Thus, it is difficult to perform, with good stability, the evaluation of the absolute value. In view of this, a mechanism is added for using as a reference signal the scan image of a standard workpiece 51 that has a pattern of certain height. An example of the standard workpiece 51 as used herein is a pattern of vertical shape with its height H0 as shown in FIG. 17. As for the material of the standard workpiece 51, it is desirable that the pattern be formed using more than two kinds of materials such as Si, W, WSi and others, for example. First, input scan image acquisition conditions such as a region or area to be observed, an observation position and others; then, acquire a scan image of the standard workpiece (at step 52 of FIG. 19). The scan image thus obtained is stored in the memory 18.

Figure 28:
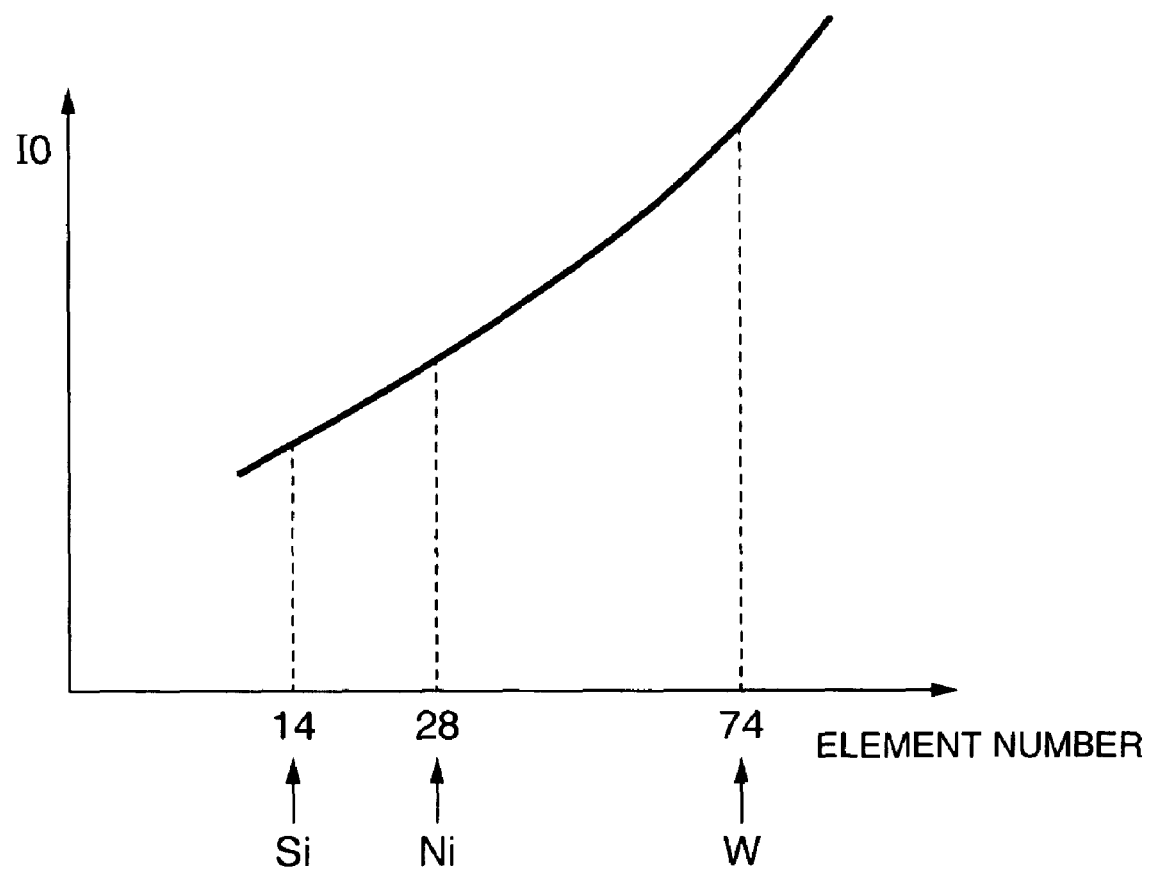
FIG. 28 is an explanation diagram showing how the value of the signal intensity I0 used in the invention varies with pattern materials.

Next, let a profile of the signal intensity of the standard workpiece be extracted to the arithmetic processor device 19, followed by measurement of a signal intensity I0 of an edge (at step 53). The signal intensity I0 of the standard workpiece is also obtainable by averaging a plurality of profiles. The standard workpiece's signal intensity I0 obtained is stored in the memory 18. At this time, the standard workpiece might be different in material from the pattern being inspected. If this is the case, the value of the signal intensity I0 is correctable in a way which follows. The intensity value I0 relies upon the element number of a pattern material as shown in FIG. 28. Once the standard workpiece is such that the value I0 is determined for Si and W, this value I0 is obtainable from the element number of the material of the inspection pattern even where the pattern is different in material from the standard workpiece.

Figure 18:
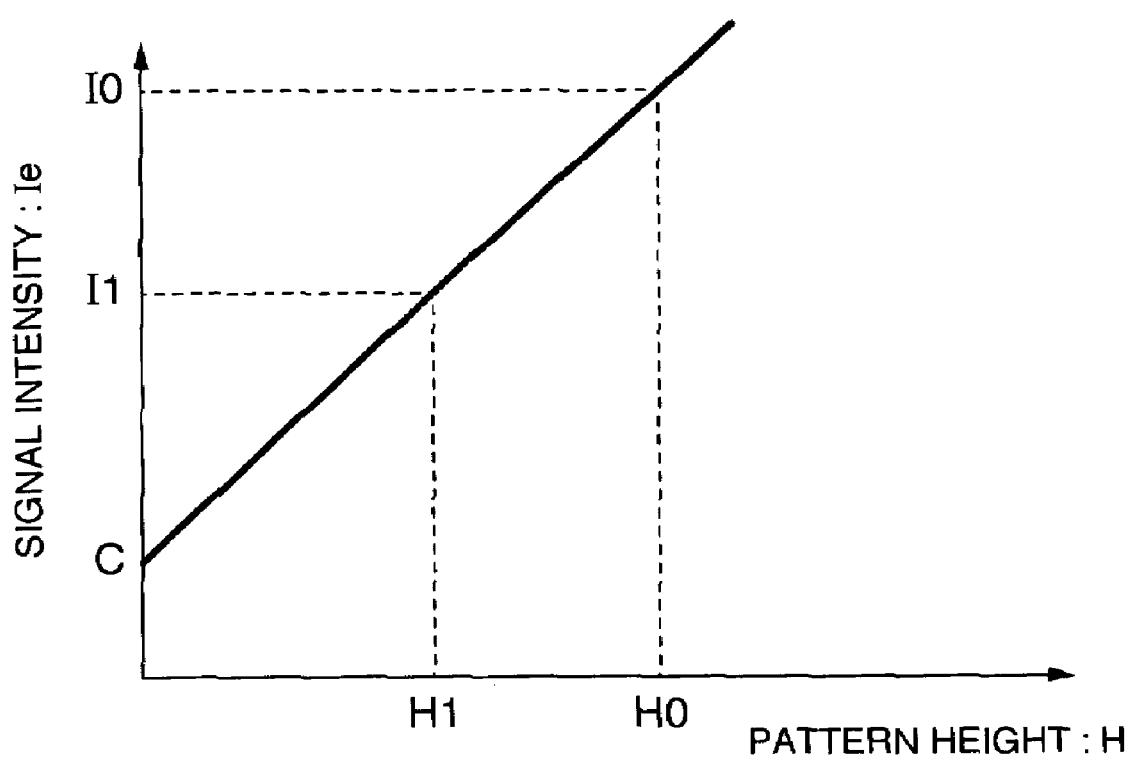
FIG. 18 is an explanation diagram showing one example of the correlation of height H of the pattern used in this invention and the signal intensity I0 of the standard workpiece.

The signal intensity I0 of the standard workpiece obtained in this way is pre-stored in the memory 18 prior to the inspection and is readable during inspection at any time. Alternatively, the signal intensity I0 of standard workpiece may be a value which is obtained by Monte Carlo simulation or else, as an example. Here, the signal intensity Ie of an edge portion also depends on the pattern height or the like. Thus, a mechanism is provided for calculating the taper angle while taking account of the pattern height. See FIG. 18, which shows one example showing the correlation of the pattern height and the signal intensity of the edge. It becomes possible to determine, from the value of signal intensity I0 of the standard workpiece with its height H0, the gradient of a straight line segment shown in FIG. 18 and then calculate the signal intensity of the edge of a pattern having any given height.

For example, the signal intensity I1 of an edge in a pattern with its height H1 is obtained as:

$$I1=(I0-C)/H0 \cdot H1+C \qquad (5)$$

Here, the constant C is determinable by the material, which is pre-storable in the memory 18. When the height of the inspection pattern is H, read out the relational equation shown in FIG. 18, which is stored in the memory unit 18 and then let the arithmetic processor device 19 calculate the signal intensity when the taper angle θ is 90° (at step 54 of FIG. 19). Note here that in case the inspection pattern is a multilayer structure of different materials, an attempt is made to calculate the I0 value for the material of a respective layer. Furthermore, calculate the values I1 and C for the height of each layer; thus, it is possible to calculate the intended value in such a way that C is added to a total sum of them. At this time, the value of C as used herein is a value C of the material of a top surface of the pattern.

Figure 19:
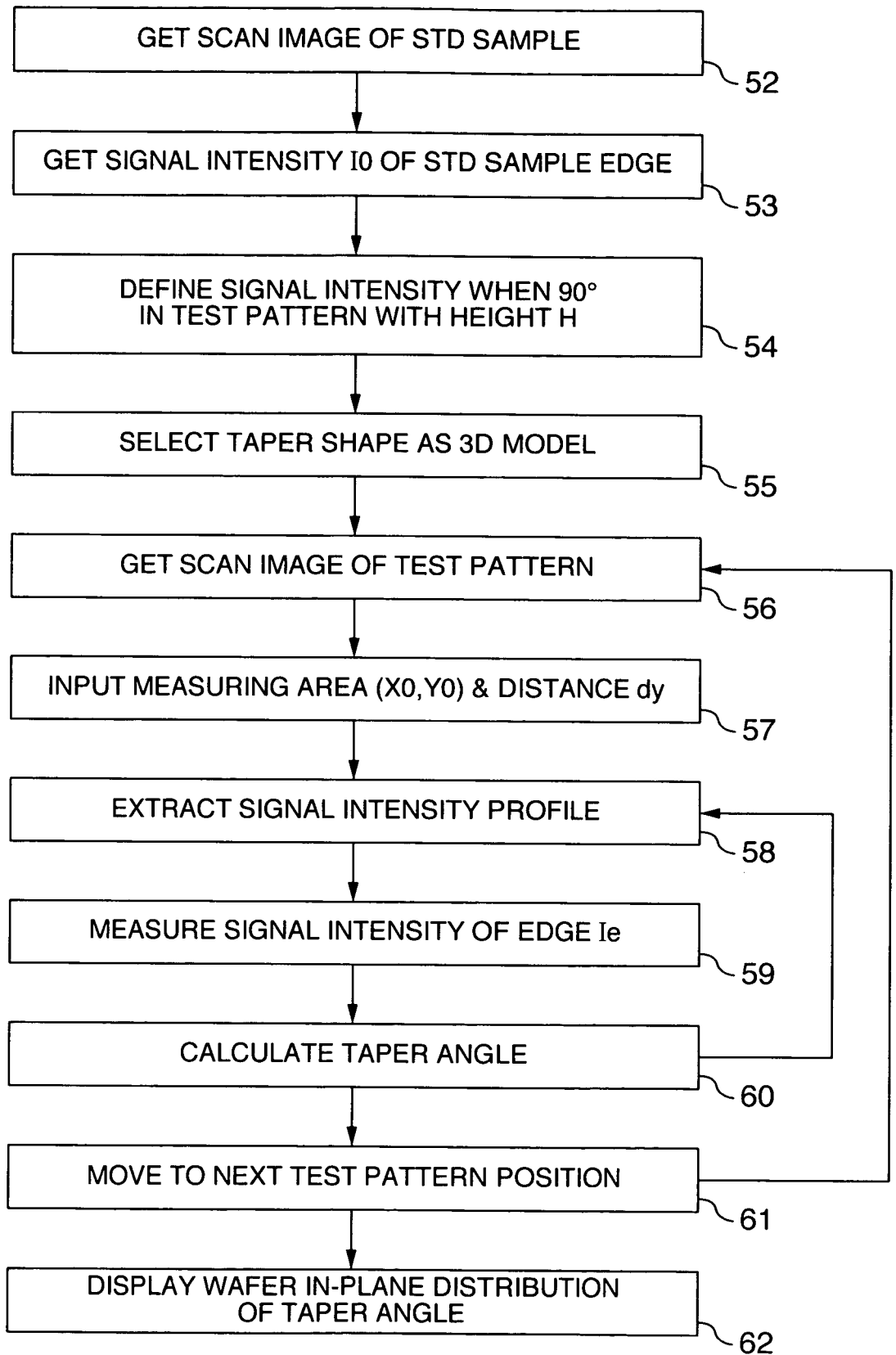
FIG. 19 shows one example of a flow of a taper angle inspection method according to the invention.

After having calculated the value I1 in this way, the next step is to select a taper shape as the kind of a stereoscopic model of the pattern to be observed (at step 55 of FIG. 19). Next, input scan image acquisition conditions such as an area being observed and an observing position; then, acquire a scan image of the area being observed (at step 56). Thereafter, upon inputting of a pattern position for length measurement and a length measurement range (X0, Y0) plus a measurement distance dy, a profile of signal intensity at Y=Y1 is extracted to the arithmetic processor device 19 as shown in FIG. 15B, by way of example (at step 58). An average value of several nearby lines in the scan image is usable as this profile of the signal intensity. Additionally, noise removal processing and averaging processing may be carried out by prior art methods.

From this profile, the signal intensity Ie was measured in regard to each of two peaks observed (at step 59). Upon determination of the signal intensity Ie, read the relation of FIG. 16 that is prestored in the memory 18 into the arithmetic processor device 19, so the taper angle θ can be obtained from the signal intensity Ie (at step 60). The taper angle θ obtained is stored in the memory 18. After having obtained the taper angle θ at Y=Y1, further extract a profile at. Y=Y1+dy (at step 58). When a stereoscopic model at a single observation position by repeated execution of this process, move to the next observation position (at 61) for acquiring a scan image (at 56). When the stereoscopic model of every pattern is obtained through repeated execution of this process, a wafer in-plane distribution of taper angles θ thus measured is visually displayed on the monitor 16 (at step 62).

It is also possible to calculate an average value and a distribution value of these feature quantities and display them. Furthermore, it becomes possible to display in a three-dimensional manner a stereoscopic structure at any given position. Further, by acquiring scan images of the standard workpiece—for example, at instants prior to and after the wafer inspection—in accordance with the stability of the electron beam inspection apparatus and then performing correction of more than one signal intensity, it becomes possible to precisely measure the taper angle while avoiding influence of per-time change of the apparatus.

It is noted that this scheme is not limited to the inspection of gate patterns and may also be applicable to the inspection and stereoscopic shape evaluation of hole patterns, wiring line patterns, groove structures such as a Cu damascene structure, magnetic heads, MEMS devices and others.

Embodiment 3

Figure 20:
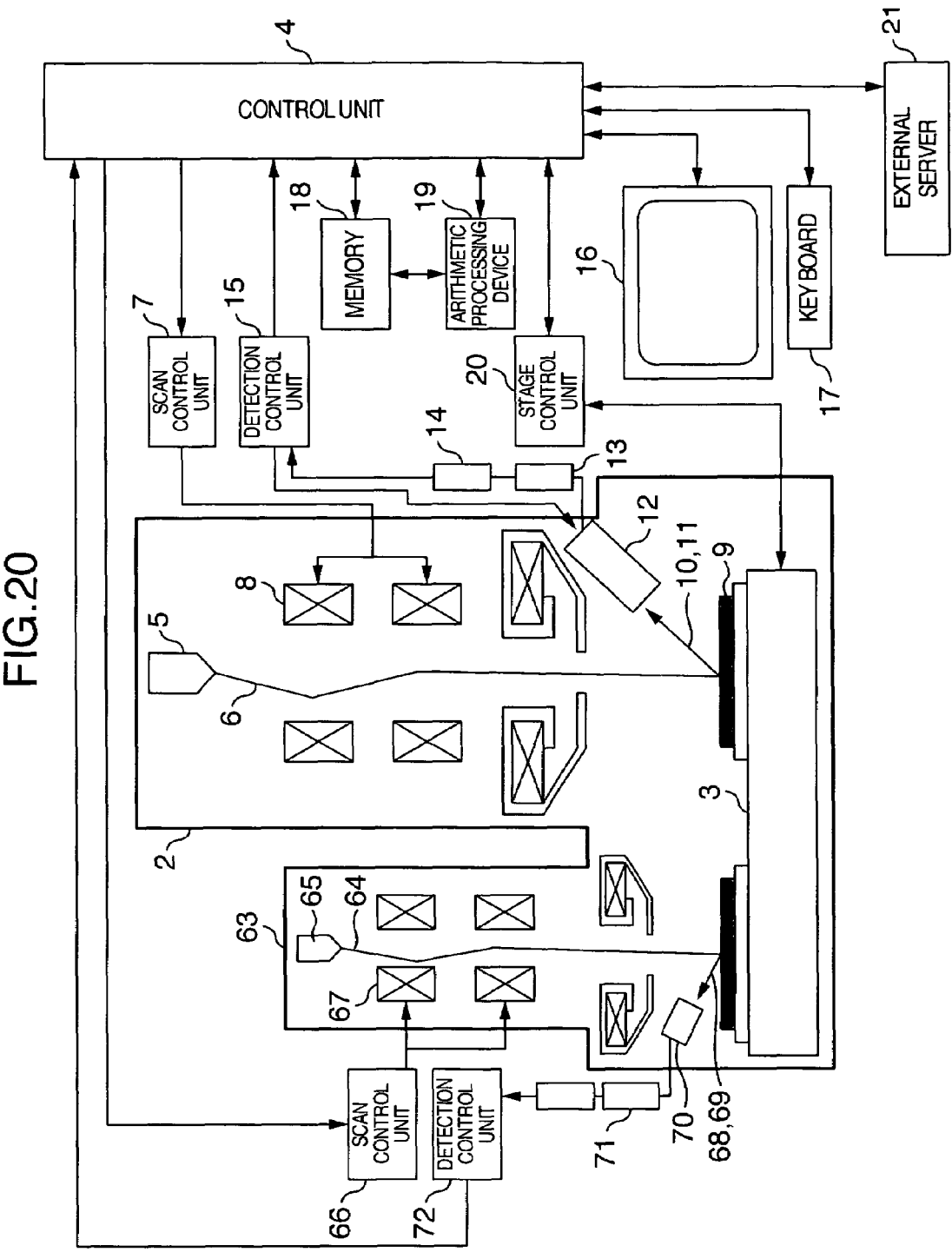
FIG. 20 is a diagram showing an exemplary configuration of a taper angle inspection apparatus of this invention as used in Embodiment 3.

In this embodiment, there will be explained another example of the taper angle inspection method of a pattern such as a gate electrode or else. In this invention, the semiconductor device inspection apparatus with the arrangement shown in FIG. 1 can be used. Alternatively as shown in FIG. 20, a scanning semiconductor device inspection apparatus with a low-acceleration electron beam 64 and a high-acceleration electron beam 6 being as incident electron beams is usable. The high-acceleration electron beam 6 that is emitted from an electron source 5 is deflected by a scanning coil 8 under the control of a scan control unit 7 and is then raster-scanned on a wafer 9. Secondary electrons 10 and backscattered electrons 11 which are generated from a surface of the wafer 9 due to the scanning of the electron beam 6 are detected by a detector 12 and then amplified by an amplifier unit 13. An amplified secondary electron signal is displayed as a scan image on a monitor 16.

On the other hand, the low-acceleration electron beam 64 leaving from an electron source 65 is deflected by a scanning coil 67 under the control of a scan control unit 66 and is then raster-scanned on a wafer 9. Secondary electrons 68 and backscattered electrons 69 that are produced from the wafer surface due to the scanning of the electron beam are detected by a detector 70 and then amplified by an amplifier unit 71. An amplified secondary electron signal is displayed as a scan image on the monitor 16. The wafer 9 is settled on a stage 3. This state 3 is controlled by a stage control unit in movement to each direction. Further, the movable stage 3 is capable of moving at any time between locations immediately beneath a high-acceleration electron optics unit 2 and a low-acceleration electron optics unit 63 in a way pursuant to wafer coordinate information as prestored in a memory 18, and has functions capable of acquiring a scan image of the low-acceleration electron beam 64 of the same portion as a scan image that was acquired by irradiation of the high-acceleration electron beam 6.

Alternatively, in the case of using the semiconductor inspection apparatus 1 with the configuration shown in FIG. 1, a scan image acquired by prior art high-acceleration SEM and each kind of information such as position data of the acquired scan image are read out of an external server 21 and/or a mobile-use storage medium and is then stored in the memory 18. An arithmetic processor device 19 can read, when the need arises, image information within the memory 18 and then perform comparative processing with an image acquired using the high-acceleration electron beam 6.

Figure 21A:
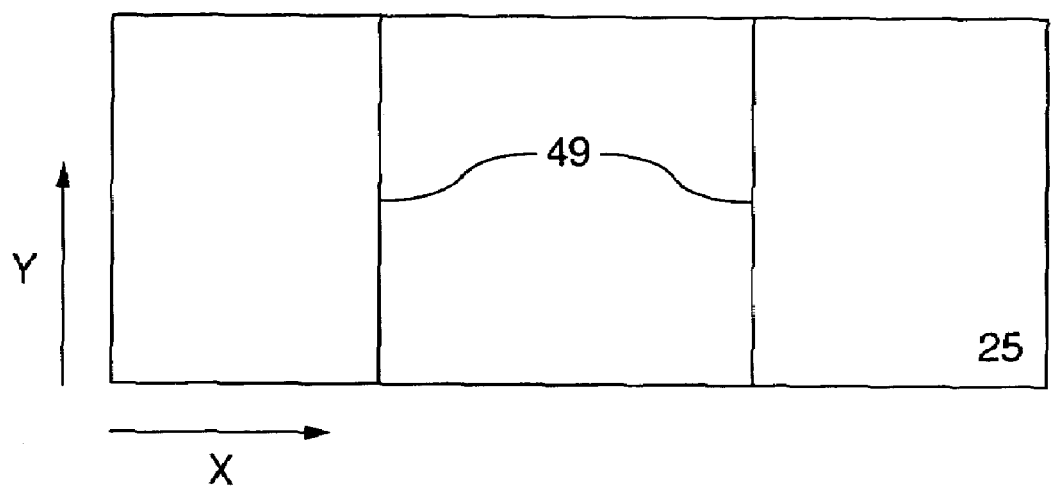
FIG. 21A shows a scan image of a taper shape due to a low-acceleration electron beam of the invention.

A method for measuring a taper angle θ by use of the apparatus shown in FIG. 20 will next be described below. First, move the wafer 9 to a location immediately underlying the low-acceleration beam 64; then, based on the position information prestored in the memory 18, acquire a scan image. The scan image acquired and the information such as position coordinates or the like are stored in the memory 18. Thereafter, move the wafer 9 to a location just beneath the high-acceleration electron optics unit 2, for acquiring a scan image by means of the high-acceleration beam 6 at the same position as that of the scan image which was acquired by the low-acceleration beam 64. The scan image acquired by the high-acceleration beam and the information such as position coordinate data or the like are stored in the memory 18. The arithmetic processor device 19 reads the scan image due to the low-acceleration electron beam 64 at the same position coordinate point and respective kinds of information items thereof along with the scan image due to the high-acceleration electron beam 6 and each kind of information item. The taper angle θ of interest is measurable by a method as will be described below. Upon acquiring of the scan image of a line pattern having a taper angle θ such as shown in FIG. 9C, irradiation of the low-acceleration beam results in acquisition of a scan image shown in FIG. 21A, wherein only edges of an upper portion 49 of the line pattern are observed.

Figure 21B:
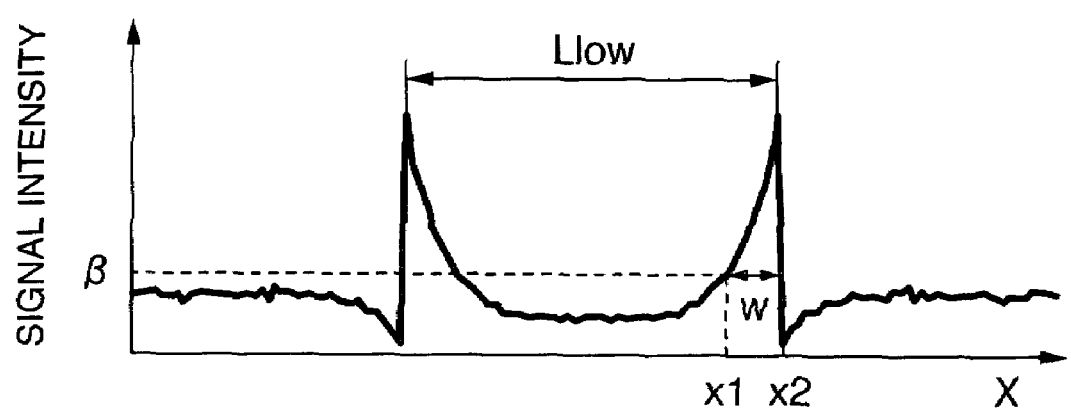
FIG. 21B shows one example of a signal profile.
Figure 22A:
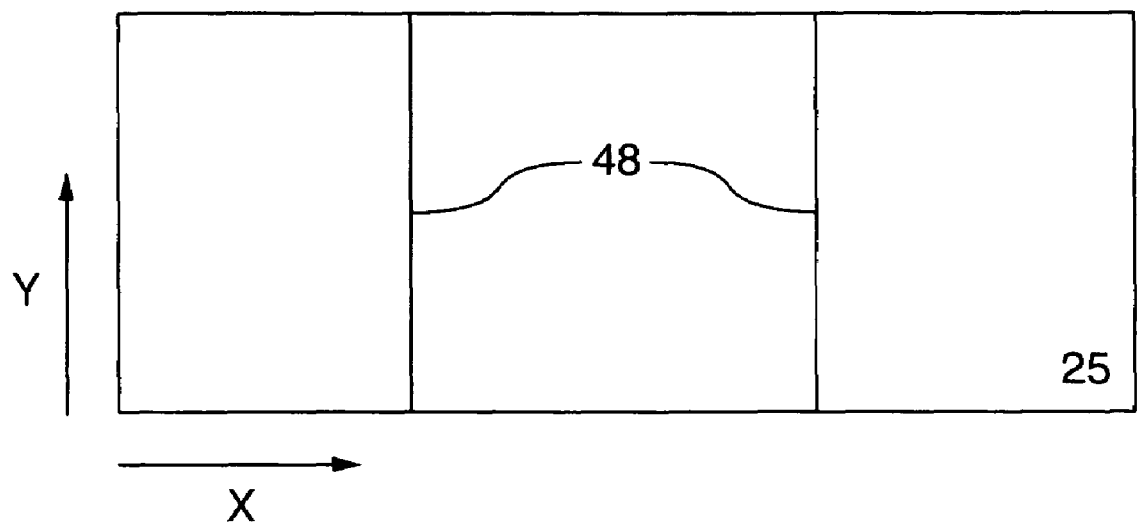
FIG. 22A shows a scan image of a taper shape due to a high-acceleration electron beam of the invention.
Figure 22B:
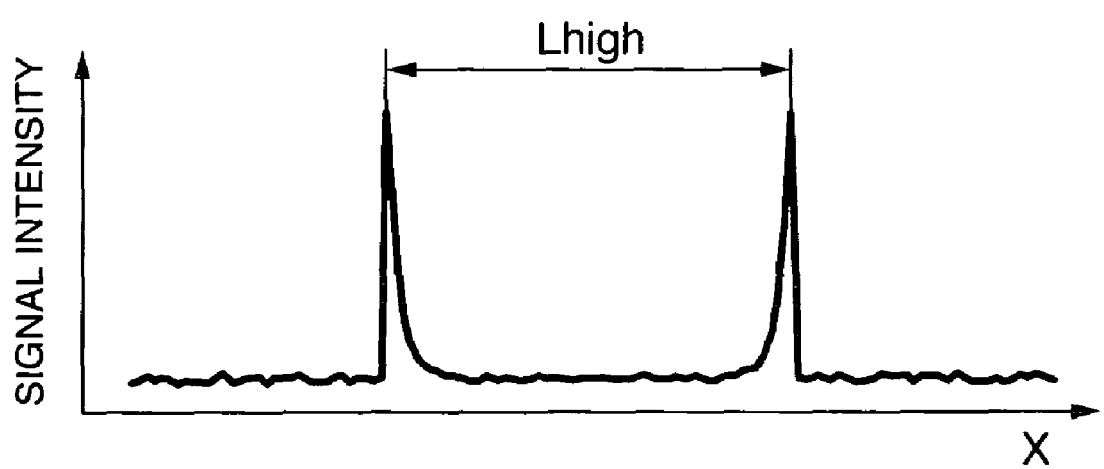
FIG. 22B shows one example of a signal profile.

A profile of the signal intensity in the X direction at this time becomes as shown in FIG. 21B. A profile of signal intensity at Y=Y1 is extracted to the arithmetic processor unit 19 for measuring a distance Llow of two peaks of this line profile. As a method for precisely obtaining the edge positions from the line profile, it is also possible to obtain it as a position having its signal intensity exceeding a predetermined threshold value β. For the high-acceleration beam, as shown in FIG. 22A, edges 48 of the line pattern are observed. A profile of signal intensity in the X direction at this time becomes as shown in FIG. 22B. The profile of signal intensity at Y=Y1 is extracted to the arithmetic processor device 18 in such a manner that it becomes the profile at the same position as the line profile which was observed by the low-acceleration beam 64; then, measure a distance Lhigh between two peaks of this line profile.

At this time, as the method for precisely obtaining the edge position from the line profile, it is also possible to obtain it as a location having its signal intensity exceeding a prespecified threshold value. See FIG. 23, which shows a relationship of the taper angle θ versus a difference between the line width Llow that was measured from the profile of signal intensity due to the low-acceleration beam 64 and the line width Lhigh measured from the profile by means of the high-acceleration beam 6. When the taper angle θ is less than 90°, the difference between the line width Llow that was measured from the profile due to the low-acceleration beam 64 and the line width Lhigh measured from the profile using the high-acceleration beam 6 becomes a constant value α.

Figure 24:
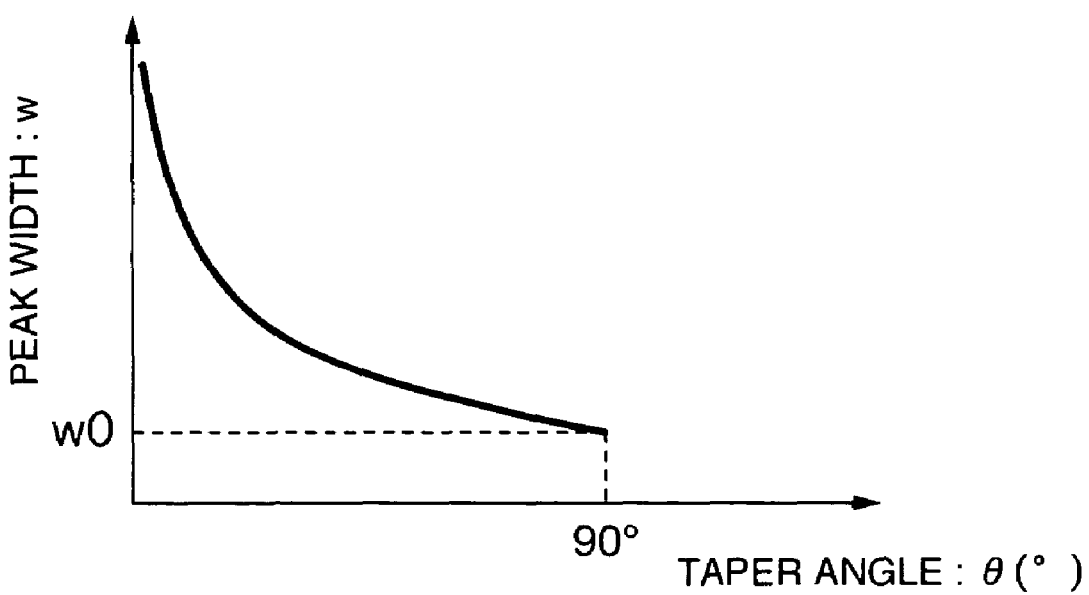
FIG. 24 is an explanation diagram showing a relationship between the width "w" of a peak of a signal profile with a forward taper shape used in the invention versus the taper angle $\theta$.

First, there will be explained one example of a method for obtaining the taper angle θ from the line profile when the taper angle θ is less than 90°—that is, in the case of a forward taper shape. At the peaks of edge portions indicated in the profile of signal intensity at Y=Y1 such as shown in FIG. 21B, a width "w" of positions x1 and x2 whereat the signal intensity becomes a certain threshold value is a difference between x1 and x2. The peak width w and the taper angle θ exhibit therebetween a relation shown in FIG. 24, which is represented by:

$$\tan\theta = T/(w-w0) \quad (6)$$

Assume that when θ=90°, the peak value w is at w0. Regarding the height H of the line pattern, it is also possible to acquire a film thickness value from the external server 21 or alternatively via storage media. As for the value w0, it is possible to obtain in advance by means of simulation or real measurement. Thus, it is possible by measurement of w from the scan image to calculate the taper angle θ at the arithmetic processor unit 19.

Figure 23:
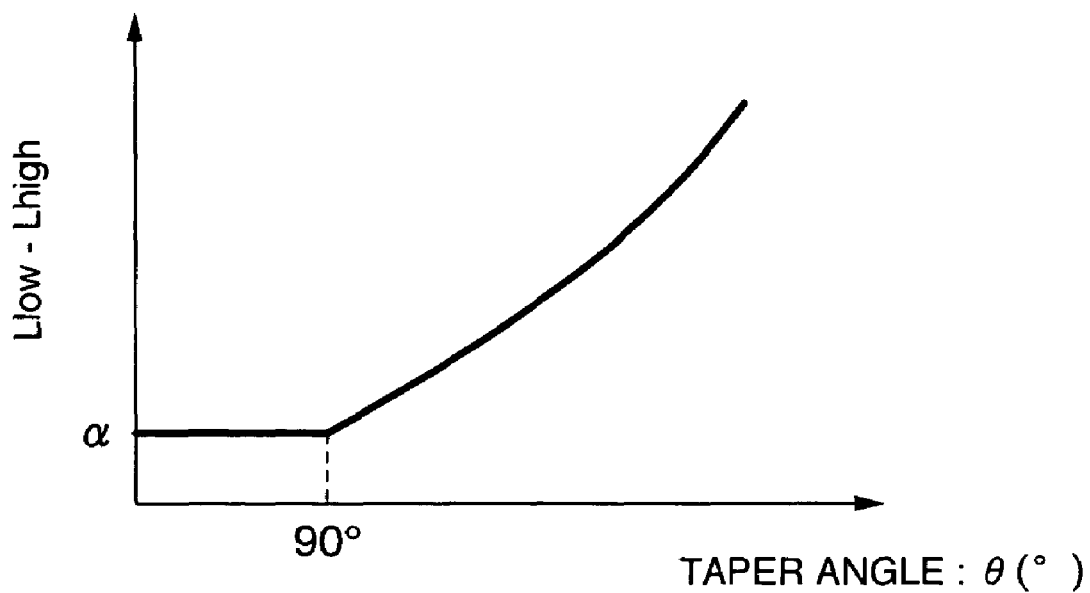
FIG. 23 is an explanation diagram showing a relationship of a difference between a line width Llow measured using the low-acceleration beam used in this invention and a line width Lhigh measured by the high-acceleration beam versus a taper angle $\theta$.

Next, an explanation will be given of a method for obtaining the taper angle θ from the line profile in case the taper angle θ is greater than 90°. The difference between the line width Llow that was measured from the profile of signal intensity due to the low-acceleration beam 64 and the line width Lhigh measured from the signal intensity profile using the high-acceleration beam 6 is dependent on the taper angle e: the greater the taper angle θ, the larger the difference. In FIG. 23, there is shown the difference between the line width Lhigh due to the high-acceleration beam and the line width Llow due to the low-acceleration beam as a function of the taper angle θ. This relation is given as:

$$\tan\theta = -(L\text{low} - L\text{high} - \alpha)/H \quad (7)$$

Note here that regarding the height H of line pattern, it is also possible to acquire a film thickness H from the external server 20 or via storage media. For the constant value a at the height H, it is possible to obtain it in advance by simulation or real measurement procedure. Concerning Llow and Lhigh, it is possible to measure each of them from the signal intensity profile of line pattern edge portion in the way stated supra. Thus it becomes possible by measurement of Llow and Lhigh from the scan image to calculate the taper angle θ in the arithmetic processor unit 19.

After having obtained the profile of signal intensity at Y=Y1 in this way, it is possible to obtain by a similar technique a taper angle θ at the next length measurement position Y=Y2. The taper angle thus obtained is stored in the memory 18. If necessary, it is possible to display on the monitor 16 a wafer in-plane distribution of the taper angles obtained.

As apparent from the foregoing, the use of this scheme makes it possible to accurately measure the taper angle while including an inverted taper shape, which is hardly measurable by the low-acceleration SEM only.

Embodiment 4

In this embodiment, another example of the taper angle inspection method of the pattern such as a gate electrode or else will be explained. In this embodiment, an explanation will be given of one example of the method for precisely measuring an angle near or around the taper angle of 90°. In this invention, the semiconductor device inspection apparatus with the configuration shown in FIG. 1 is usable.

When emitting a high-energy electron beam 35 onto a pattern having its taper angle 33 as shown in FIG. 9C, a great number of secondary electrons 10 and backscattered electrons 11 are generated by the edge effect from the pattern's sidewall 48 in the way described in conjunction with Embodiment 2. When forming a scan image of the pattern of FIG. 9C from these secondary signals, sidewall portions 48 of the pattern are observed brightly as shown in FIG. 15A. A line profile of signal intensity of the scan image shown in FIG. 15A is shown in FIG. 15B. In the case of the taper angle of 90° or more or less, the signal intensity Ie of sidewall portion 48 is significantly dependent on the taper angle θ so that it is possible to measure with high precision the taper angle θ from the signal intensity of sidewall 48.

Figure 29A:
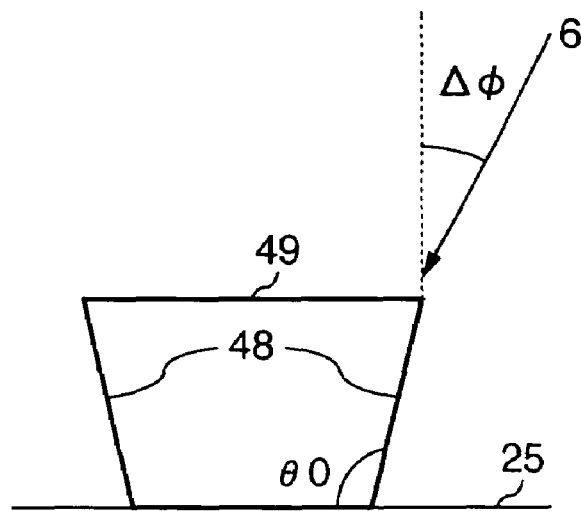
FIGS. 29A and 29B show one example of the correlation of the signal intensity Ie of an edge portion on a wafer with its taper angle $\theta$ and an incidence angle $\Delta\phi$ of an electron beam, which is used in the invention.
Figure 29B:
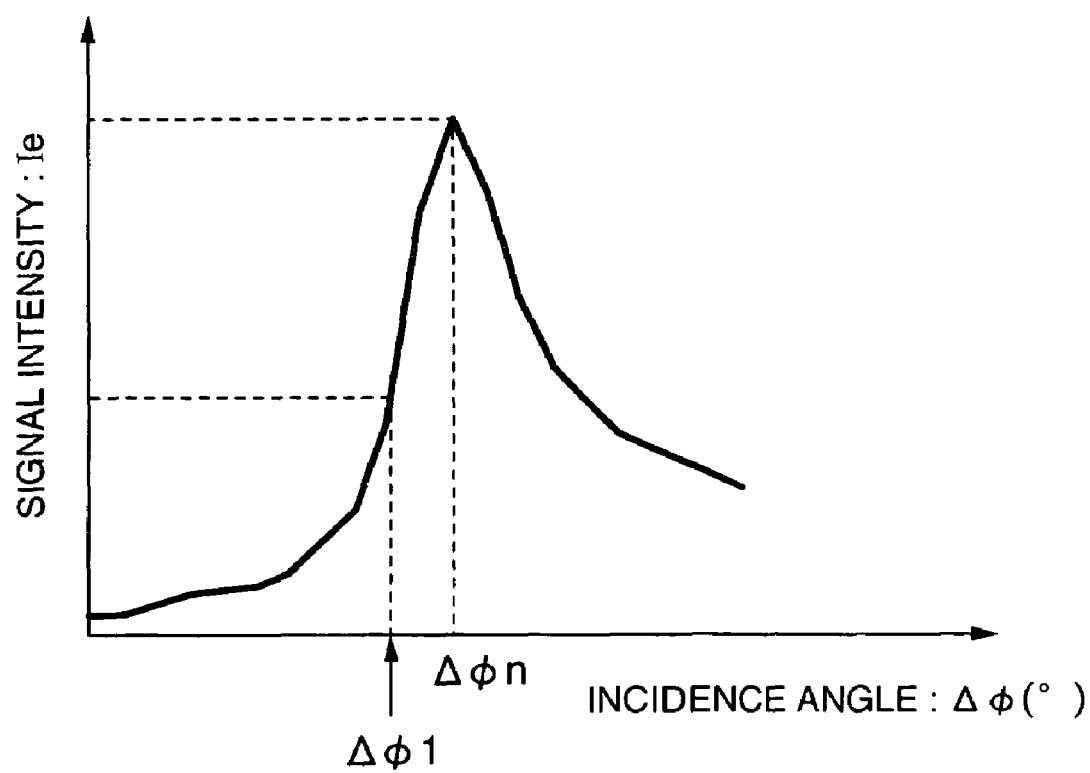

FIGS. 29A and 29B indicate one example showing a correlation of the signal intensity Ie of an edge portion at a wafer with its taper angle of θ0 and the incidence angle Δφ of the electron beam. FIG. 29A shows the correlation of the taper angle θ0 and the incidence angle Δφ whereas FIG. 29B shows the correlation of the signal intensity Ie and the incidence angle Δφ. When the incoming direction of the electron beam 6 becomes identical to the direction of the taper, that is, when the electron beam 6 is emitted along the pattern sidewall 48, the signal intensity Ie becomes maximal. In this embodiment, the taper angle θ is obtained from the relationship of the incidence angle Δφ of electron beam 6 and the signal intensity Ie of secondary electrons 10 and backscattered electrons 11 at the time the electron beam 6 is guided to fall onto a wafer 9 while deflecting it to have the incidence angle Δφ.

First, the electron beam 6 emitted from the electron source 5 is deflected by the scanning coil 8 that is controlled by the scan control unit 7 and is raster-scanned on the wafer 9. At this time, the incidence angle of the electron beam emitted is set at a specific angle which is deflected by Δφ1 from the vertical direction of the wafer. A secondary electron signal of secondary electrons 10 and backscattered electrons 11, which are generated from the wafer 9 by irradiation of the electron beam 6, is detected by the detector 12 and then amplified by the amplifier unit 13. An amplified signal is converted by the converter 14 to corresponding digital data, which is transferred to the control unit 4 and then stored in a memory 18. At this time, the electron beam 6's irradiation conditions such as the incidence angle Δφ1 are also stored in the memory 18 simultaneously.

Furthermore, the electron beam 6 is deflected by a control coil 8 under the control of the scan control unit 7 to have an angle that is deflected by Δφ2; then, the beam is raster-scanned on the wafer 9. Those secondary electrons 10 and backscattered electrons 11 generated are detected by the detector 13, amplified, converted, and then sent to the control unit 4, followed by storage in the memory 18. Repeating this procedure results in acquisition of a scan image in the vicinity of the incidence angle of 90°. Next, the arithmetic processor device 19 uses the acquired scan image to measure the signal intensity Ie of an edge portion, and then measure the incidence angle dependency of the signal intensity Ie at the same location on the wafer 9. For example, in case a relationship shown in FIGS. 29A-29B is obtained as the incidence angle dependency of the signal intensity Ie, it was possible to precisely calculate a taper angle θ0 from an incidence angle Δϕn of the electron beam 6 when a maximal value of Ie is obtained.

Embodiment 5

Figure 9D:
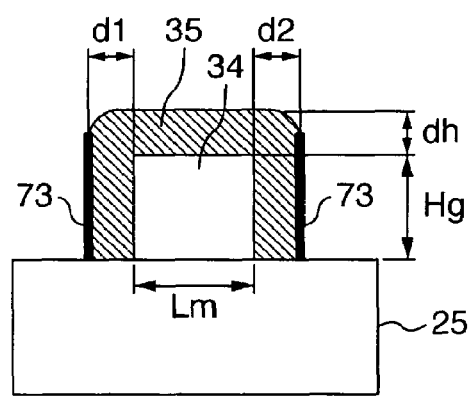

In this embodiment, one example will be explained of a method for simultaneously inspecting, in a pattern such as a gate part of a MOS device or the like as shown in FIG. 9D, the shape of an outside edge of a spacer 35 and that of an edge of a buried metallic film 34 and for non-destructively inspecting both the width Lm of the metal film and the widths d1 and d2 of an insulating film formed on the metal film at a time. In this invention, the semiconductor inspection apparatus arranged as shown in FIG. 1 is usable.

Let a high-energy electron beam 6, fall onto the pattern with a spacer 35 of insulating film being formed on the buried gate electrode 34 as shown in FIG. 9D. This scheme is employable in cases where certain metal elements such as W, Co, Ni and the like are contained in a material of the gate electrode 34, for example, when W, WSi, Ni, NiSi or else is used as the material of the gate electrode 34. Alternatively, this scheme is also applicable to the case where chemical compound containing therein a heavy metal element such as NiSi, CoSi, TiSi or else is formed on the gate electrode. Upon irradiation of the high-energy electron beam 6 onto a wafer 9 having such the gate electrode 34, secondary electrons 10 and backscattered electrons 11 are produced from a substrate surface, resulting in a large number of secondary electrons 10 and backscatter electrons 11 being generated by the edge effect from sidewalls 73 of the spacer 35.

At this time, the number of the backscatter electrons 11 leaving from the gate electrode 34 becomes greater than the number of the backscatter electrons from the other spacer 35 part. Thereafter, when the backscatter electrons 11 from the gate electrode 34 escape from the surface, secondary electrons are released from the surface. Thus, those backscatter and secondary electrons to be detected by the detector 12 upon irradiation of the electron beam 6 to an upper face of the gate electrode 34 becomes greater in number. As a result, it is possible to observe the buried gate electrode 34. An example of such irradiation energy may be an electron beam of about 30 keV to 100 keV—that is, more than or equal to 30 keV but less than or equal to 100 keV—is usable in case the insulating film on the gate electrode has its film thickness "dh" of 400 nanometers (nm) or less. When the thickness dh of the insulator film on the gate electrode ranges from 400 nm to 100 μm, it is possible to use an electron beam of about 50 to 200 keV.

Figure 26:
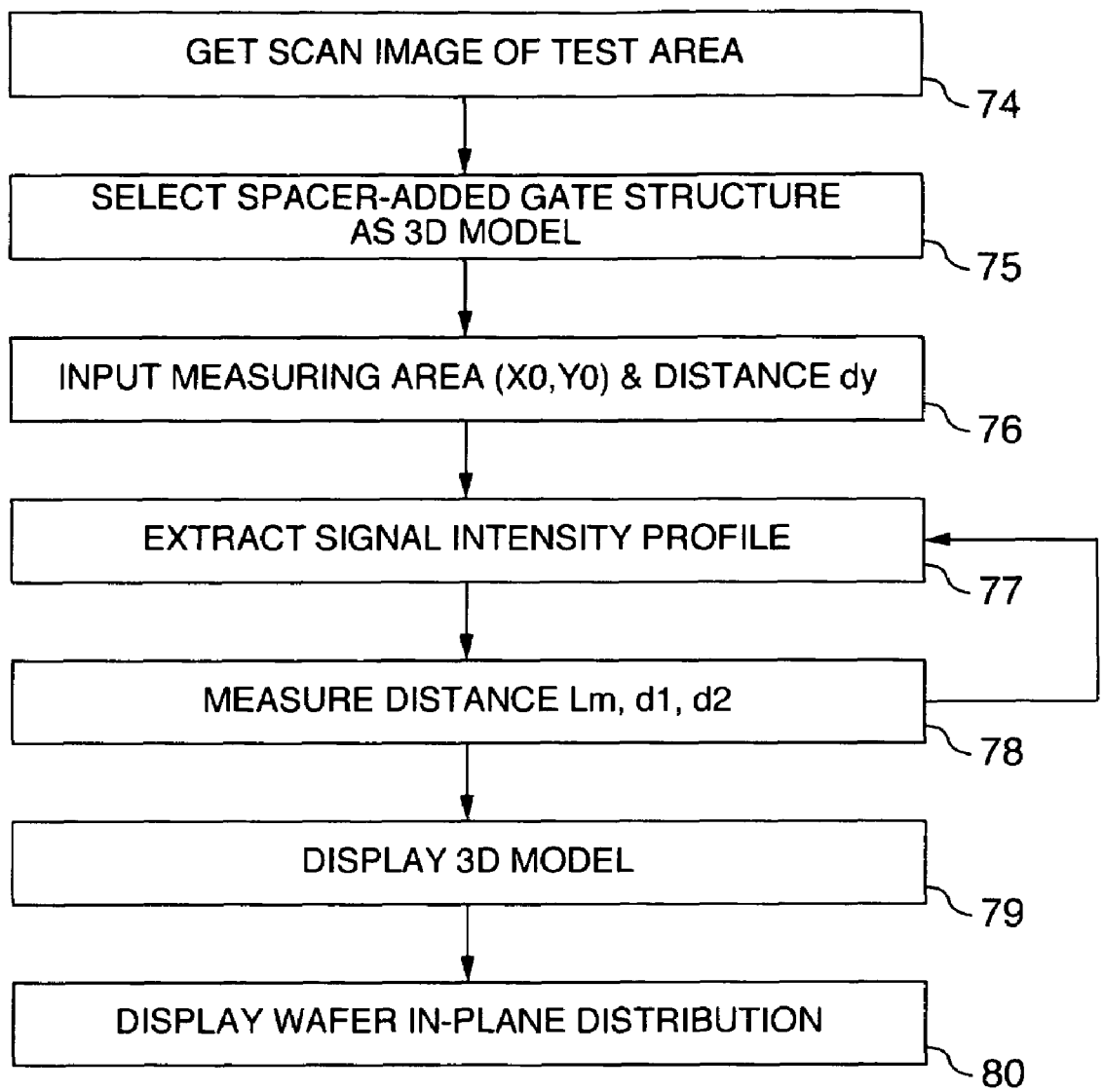
FIG. 26 is one example of a flow of a method for inspecting the spacer-added gate structure according to the invention.

In this embodiment, an exemplary length measuring method of the gate structure shown in FIG. 9D will be explained as one example of the length measurement method of the gate structure with the spacer 35 added thereto in accordance with a flow shown in FIG. 26. Firstly, input scan image acquisition conditions such as a region or area to be observed and an observation position or the like, thereby acquiring a scan image of the observation area (at step 74).

Figure 25A:
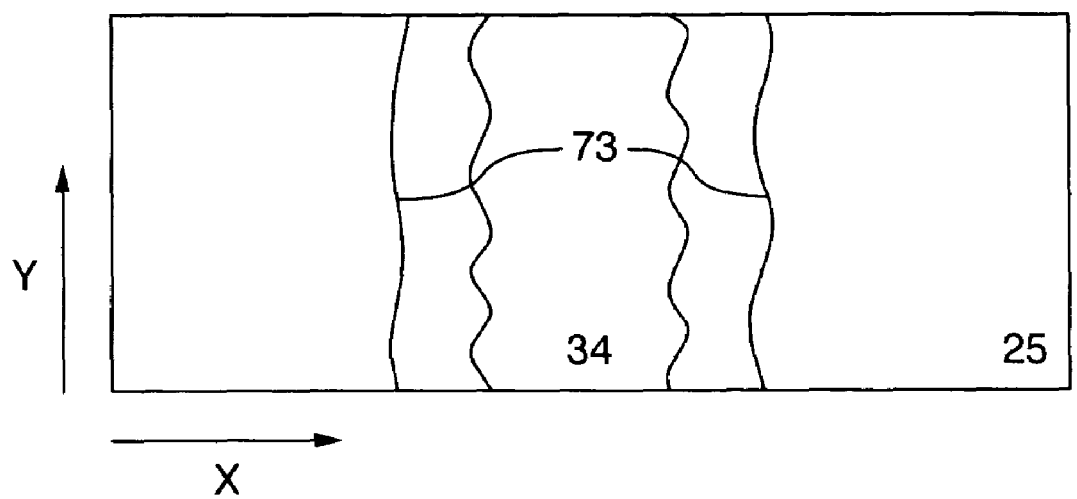
FIG. 25A is an explanation diagram showing a scan image of a spacer-added gate structure according to the invention.
Figure 25B:
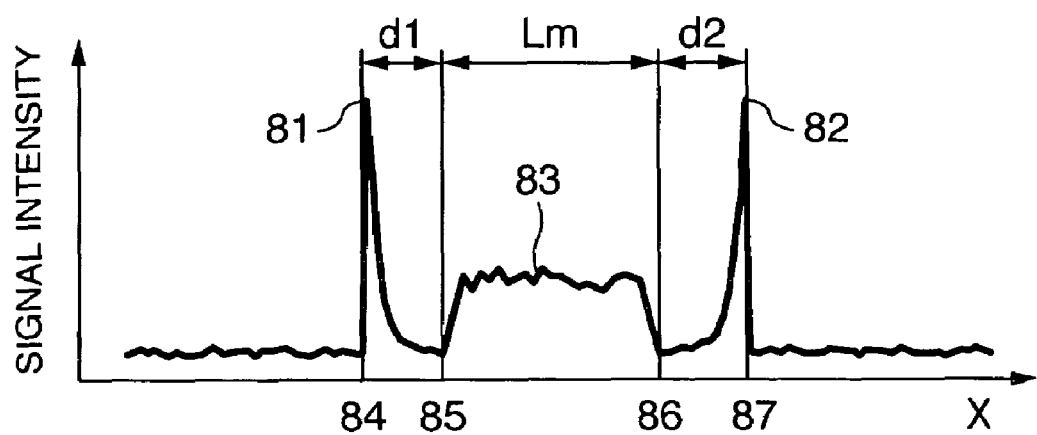
FIG. 25B shows an exemplary signal profile.

At this step, a scan image such as shown in FIG. 25A for example is obtained. In this scan image, the spacer's sidewalls 73 and the buried gate electrode 34 are observed. Next, select the kind of a stereoscopic model of the observed pattern—for example, in this embodiment, select the spacer-added gate electrode structure (at step 75). Upon inputting of a length measurement range (X0,Y0) and a measuring distance dy (at step 76), a profile of signal intensity at Y=Y1, for example, is extracted to the arithmetic processor device 19 as shown in FIG. 25B (at step 77). An example of this profile of signal intensity as used herein is an average value of several nearby lines in the scan image. Where necessary, noise removal processing and averaging processing may be carried out by known methods.

In this profile, peaks 81 and 82 due to the spacer sidewalls 73 and a peak 83 due to the gate electrode were observed. From this signal intensity, the intended length measurement was done; more specifically, it was possible to measure d1 from a rising position 84 of the peak 81 and a one rising position 85 of the peak 83, while measuring d2 from a rising position 86 of the peak 83 and a rising position 87 of the peak 82. It was also possible to measure the gate electrode width Lm from the rising positions 85 and 86 at both ends of the peak 83 (at step 78). After having obtained the spacer width values d1 and d2 at Y=Y1 along with the gate electrode width Lm in this way, further extract a profile at Y=Y1+dy (at step 77). Repeating this procedure results in the spacer widths d1-d2 and gate electrode width Lm being obtained at every length measurement position.

After having calculated the spacer widths d1-d2 and gate electrode width Lm at every measurement position, it is possible to generate a stereoscopic model at the arithmetic processor unit 19 and then display a stereoscopic structure on the monitor 16 in a 3D fashion (at step 79). In regard to the gate electrode height Hg and the thickness dh of the insulator film on the gate electrode, it is possible to acquire a film thickness measurement value prior to pattern formation by way of the external server 21 or alternatively via storage media. It is also possible to display on the monitor 16 a cross-sectional structure at any given position. It is further possible to display a wafer in-plane distribution of the feature quantities of Lm, d1 and d2 (at step 80) and to perform alarm display when any one of them exceeds a preset allowable value.

Figure 27:
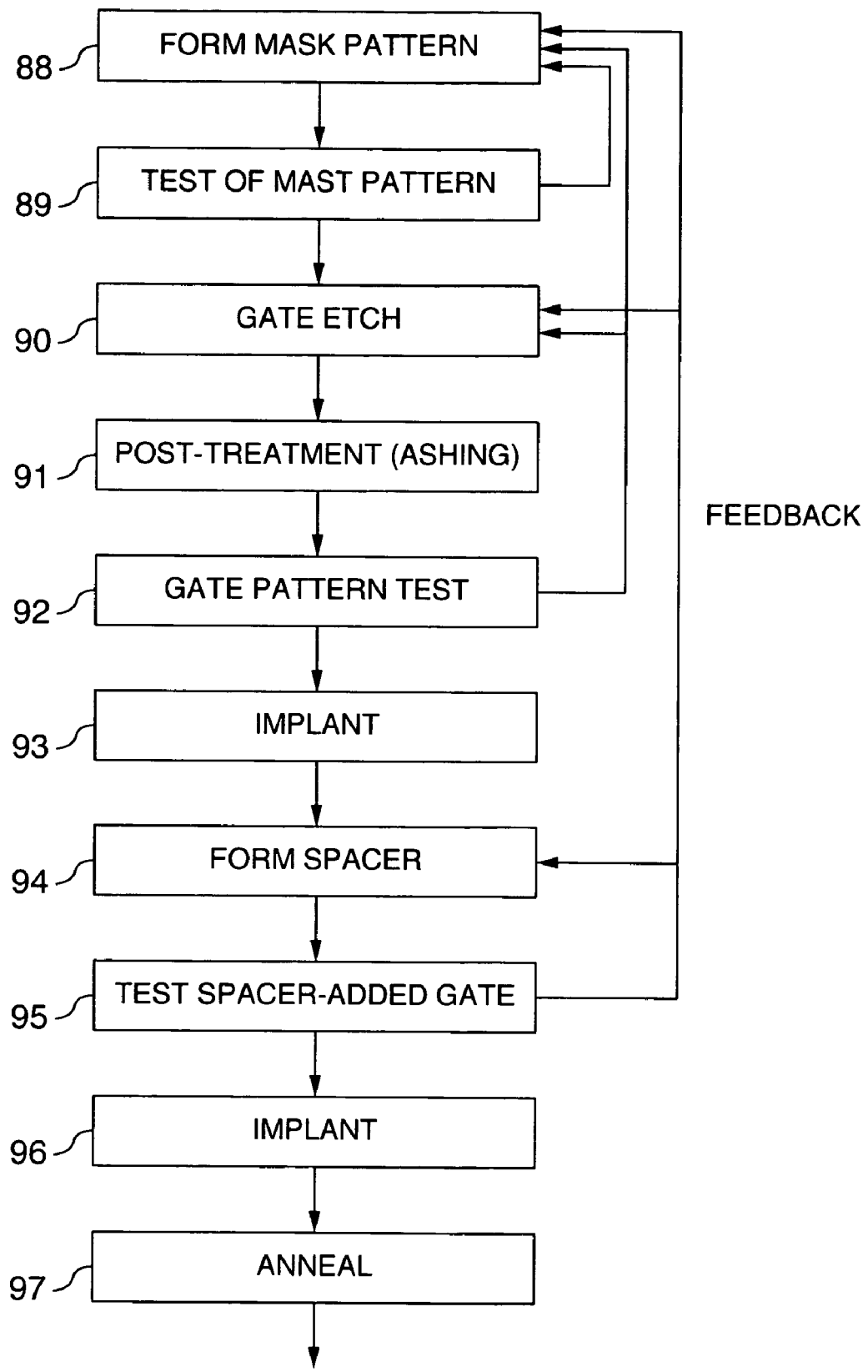
FIG. 27 shows one example of an evaluation flow at the time the invention is applied to an inspection procedure during a semiconductor device fabrication process.

Turning to FIG. 27, there is shown one example of an evaluation flow when this embodiment is applied to the inspection during a semiconductor device fabrication process. First, form a patterned mask on a gate electrode material and a mask material (at step 88). Thereafter, perform inspection of the mask pattern (at step 89). At this time, the inspection is achievable while applying the shape of the mask's taper angle or else to either Embodiment 2 or Embodiment 3. Depending on a test result, it is possible to perform feedback to the semiconductor device fabrication process while appropriately varying exposure conditions of a lithography process, for example. After completion of the mask patterning, apply dry etching to the gate electrode and the mask material to thereby form a pattern (at step 90).

Thereafter, post-treatment such as mask removal and cleaning or else is done (at step 91). Then, perform inspection of the gate electrode and mask pattern (at step 92). At this time, the inspection is achievable by applying the gate electrode's taper angle and notch shape to Embodiment 1 or Embodiment 2 or Embodiment 3. From these inspection results, it is possible to perform feedback to the semiconductor fabrication process while varying the dry etching conditions or the like, for example. Thereafter, cleaning is done when the need arises; then, perform implantation (at 93). Thereafter, form an insulator film on the gate electrode; then, perform dry etching to form a spacer (at 94). Next, the gate inspection shown in this embodiment was carried out (at 95).

This embodiment is applicable to samples with a spacer such as an insulator film or else being formed on or above such the gate electrode. From the inspection results of the gate electrode width and spacer width, it is possible to perform feedback to the semiconductor device manufacturing process while changing major process conditions—for example, the spacer forming conditions, spacer etch conditions, gate electrode dry-etch conditions and mask forming process conditions and others. Thereafter, by way of cleaning and implantation processes (at step 96), annealing is done for activation of implanted regions (at 97).

Performing this anneal processing (97) makes it possible to recover or "cure" electron ray irradiation damages occurred during the inspection using the high-acceleration electron beam. This annealing (97) is the process that is ordinarily performed in semiconductor device fabrication processes for activation of dopants implanted after implantation. By performing the inspection using the high-acceleration electron beam prior to this annealing (97), it becomes possible to perform the inspection while eliminating the influence of damages due to electron ray irradiation without having to add any processing for curing such electron ray irradiation damages.

Embodiment 6

In a semiconductor device inspection method for performing size measurement between a length measurement starting point and an ending point of a scan image obtainable by scanning a focused electron beam on a wafer, this method includes the steps of emitting an electron beam having an energy capable of penetrating a part of a workpiece and reaching an unexposed portion with respect to the electron beam, generating a scan image based on a secondary signal generated by irradiation of the electron beam, detecting, from a signal thus obtained, position information of a pattern to be inspected and a signal intensity, generating a stereoscopic model of the pattern to be inspected, using the detected position information and signal intensity to calculate a feature quantity of the pattern to be inspected, constructing a stereoscopic structure from the calculated feature quantity of the pattern, and displaying a three-dimensional structure of the stereoscopic structure thus constructed.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A semiconductor inspection apparatus having a length measurement function for performing size measurement between a measurement start point and an end point of a scan image obtainable by scanning a focused electron beam on a wafer, said apparatus comprising:
   means for emitting an electron beam with a constant sustained angle of incidence with respect to a workpiece having an energy capable of penetrating a part of the workpiece and reaching an unexposed portion;
   means for generating a scan image based on a secondary signal generated by irradiation of the electron beam with the constant sustained angle of incidence with respect to the workpiece;
   means for detecting, from the secondary signal thus obtained, position information of a pattern to be inspected and a signal intensity;
   means for generating a stereoscopic model of the pattern to be inspected;
   means for using the position information and the signal intensity thus detected to calculate a feature quantity of a shape of the pattern to be inspected;
   means for constructing a stereoscopic structure from the feature quantity of the pattern calculated; and
   means for displaying a three-dimensional structure of the stereoscopic structure thus constructed.

2. The semiconductor inspection apparatus according to claim 1, further comprising:
   means for controlling the electron beam with the constant sustained angle of incidence with respect to the workpiece for irradiation so that the energy thereof is more than or equal to 10 keV and yet less than or equal to 200 keV.

3. The semiconductor inspection apparatus according to claim 1, wherein said feature quantity to be calculated is a taper angle of the pattern being inspected.

4. The semiconductor inspection apparatus according to claim 1, wherein said feature quantity to be calculated is a width of a pattern buried in the pattern being inspected.

5. The semiconductor inspection apparatus according to claim 1, wherein said feature quantity to be calculated is a distance between a pattern buried in the pattern to be inspected and an edge portion of a surface of the pattern being inspected.

6. The semiconductor inspection apparatus according to claim 1, wherein the feature quantity to be calculated includes a width of a pattern at a notch portion of the workpiece.

7. The semiconductor inspection apparatus according to claim 1, further comprising:
   means for performing alarm display when the calculated feature quantity exceeds a preset value.

8. A semiconductor inspection apparatus having a length measurement function for performing size measurement between a measurement start point and an end point of a scan image obtainable by scanning a focused electron beam on a wafer, said apparatus comprising:
   means for emitting a first electron beam with a first constant sustained angle of incidence with respect to a workpiece having a first energy capable of penetrating a part of a workpiece and reaching an unexposed portion;
   means for emitting a second electron beam with a second constant sustained angle of incidence with respect to the workpiece having a second energy capable of arriving only at a top surface of the workpiece at a same position as an irradiation position of said first electron beam with the first constant sustained angle of incidence having the first energy;
   means for using a first secondary signal generated by irradiation of said first electron beam with the first constant sustained angle of incidence having the first energy and a second secondary signal generated by irradiation of said second electron beam with the second constant sustained angle of incidence having the second energy to detect position information of an edge of a pattern to be inspected and a signal intensity;

means for generating a stereoscopic model of the pattern to be inspected;

means for using the detected information to calculate a feature quantity of the pattern being inspected;

means for constructing a stereoscopic structure from the calculated feature quantity of the pattern; and means for displaying a three-dimensional structure of the stereoscopic structure thus constructed.

9. A semiconductor inspection apparatus having a length measurement function for performing size measurement between a length measurement start point and an end point of a scan image obtainable by scanning a focused electron beam on a wafer, said apparatus comprising:

means for emitting an electron beam having an energy capable of penetrating a part of a workpiece and reaching an unexposed portion;

deflection means for deflecting an incidence angle of said electron beam to generate an electron beam with a constant sustained angle of incidence with respect to the workpiece;

means for generating a scan image based on said secondary signal generated from the workpiece by irradiation of the electron beam with the constant sustained angle of incidence;

means for detecting, from a signal thus obtained, position information of a pattern to be inspected and a signal intensity;

means for generating a stereoscopic model of the pattern to be inspected;

means for using the detected position information and signal intensity along with a deflection angle of the electron beam to calculate a feature quantity of a shape of the pattern being inspected;

means for constructing a stereoscopic structure from the calculated feature quantity of the pattern; and means for displaying a three-dimensional structure of the stereoscopic structure thus constructed.

* * * * *